(12) United States Patent
Bryant, Jr.

(10) Patent No.: US 11,554,184 B2
(45) Date of Patent: Jan. 17, 2023

(54) SYNTHETIC CANNABINOID COMBINATION THERAPY COMPOSITIONS AND METHODS FOR PERSONALIZED AND TARGETED THERAPIES INCLUDING THE TREATMENT OF INFECTIOUS DISEASES

(71) Applicant: Vyripharm Enterprises, Inc., Houston, TX (US)

(72) Inventor: Jerry L. Bryant, Jr., Bellaire, TX (US)

(73) Assignee: Vyripharm Enterprises, Inc., Houston, TX (US)

( * ) Notice: Subject to any disclaimer, the term of this patent is extended or adjusted under 35 U.S.C. 154(b) by 0 days.

(21) Appl. No.: 17/697,416

(22) Filed: Mar. 17, 2022

(65) Prior Publication Data

US 2022/0305147 A1 Sep. 29, 2022

Related U.S. Application Data

(60) Provisional application No. 63/166,866, filed on Mar. 26, 2021.

(51) Int. Cl.
*A61K 51/00* (2006.01)
*A61M 36/14* (2006.01)
*A61K 51/04* (2006.01)

(52) U.S. Cl.
CPC .............................. *A61K 51/0497* (2013.01)

(58) Field of Classification Search
CPC ................................................ A61K 51/0497
See application file for complete search history.

(56) References Cited

U.S. PATENT DOCUMENTS

| | | |
|---|---|---|
| 4,837,312 A | 6/1989 | Dervan et al. |
| 7,142,988 B1 | 11/2006 | Johnson |
| 2005/0095582 A1 | 5/2005 | Gillim-Ross et al. |
| 2009/0105128 A1 | 4/2009 | Bornhop et al. |
| 2010/0119606 A1 | 5/2010 | Whittle et al. |
| 2010/0286993 A1 | 11/2010 | Lovelace |
| 2011/0117014 A1 | 5/2011 | Norenberg |
| 2012/0156134 A1 | 6/2012 | Squires |
| 2016/0184459 A1 | 6/2016 | Ueki et al. |
| 2017/0107247 A1 | 4/2017 | Gunning et al. |
| 2017/0199168 A1 | 7/2017 | Jackson, Jr. et al. |
| 2018/0285810 A1 | 10/2018 | Ramachandran et al. |
| 2018/0308046 A1 | 10/2018 | Schutt |
| 2020/0085978 A1 | 3/2020 | Kuo et al. |
| 2021/0080441 A1 | 3/2021 | Bryant, Jr. et al. |

FOREIGN PATENT DOCUMENTS

| | | |
|---|---|---|
| EP | 2992880 A1 | 3/2016 |
| EP | 2992882 A1 | 3/2016 |
| JP | 2009534381 A | 9/2009 |
| WO | 2005009479 A1 | 2/2005 |
| WO | 2005117997 A1 | 12/2005 |
| WO | 2016046793 A2 | 3/2016 |
| WO | 2017196655 A1 | 11/2017 |
| WO | 2019018536 A1 | 1/2019 |

OTHER PUBLICATIONS

Xiangyang Liang et al., "Cyclam complexes and their applications in medicine", Chem. Soc. Rev., 2004, vol. 33, p. 246-266 DOI:10.1039/b313659k (see sections 1, 4, especially 4.3.1 on pp. 259-260).
Frau S., et al., "Pyrazole-Type Cannabinoid Ligands Conjugated with Fluoro-Deoxy-Carbohydrates as Potential PET-Imaging Agents: Synthesis and CB1/CB2 Receptor Affinity Evaluation," Journal of Fluorine Chemistry, Elsevier, NL, vol. 152, Mar. 18, 2013, pp. 166-172.
International Search Report and Written Opinion for PCT Application No. PCT/US2022/021765, dated Jun. 14, 2022, 8 pages.
International Search Report and Written Opinion for PCT Application No. PCT/US2022/021772, dated Jun. 14, 2022, 6 pages.
International Search Report and Written Opinion for PCT Application No. PCT/US2022/021774, dated Jun. 14, 2022, 6 pages.
English Translation of JP 2009534381, 20 pages.
Dessolin et al; "Tri-N-Boc-Tetraazamacrocycle-Nucleoside Conjugates: Synthesis and anti-HIV activities"; Nucleosides and Nucleotides; Aug. 21, 2006; vol. 17, pp. 957-968; p. 958.
Schmid, M., et al., "Synthesis and evaluation of a radiometal-labeled macrocyclic chelator-derivatised thymidine analog," Nuclear Medicine and Biology, vol. 33, pp. 359-366 (2006).
Tsao, N. et al., "99mTc-N4amG: Synthesis biodistribution and imaging in breast tumor-bearing rodents," Appl. Radiat. Isot., vol. 72, pp. 1-20 (2013).

*Primary Examiner* — Michael G. Hartley
*Assistant Examiner* — Melissa J Perreira
(74) *Attorney, Agent, or Firm* — Polsinelli PC; Ron Galant

(57) ABSTRACT

Compositions and methods for the personalized and targeted therapeutic treatment of diseases and disorders, including the treatment of pain, inflammation, and infectious diseases in a subject. In particular, labeled synthetic cannabinoid therapeutic compositions are provided that include a conjugate of a synthetic cannabinoid compound, a chelator, and a label, that when coupled with imaging may be used to determine in real time optimal dosing and targeting of particular pathways and tissues to provide personalized therapies. Combination therapies are also provided that include one or more synthetic cannabinoid compound and at least one active pharmaceutical ingredient.

6 Claims, 2 Drawing Sheets

SYNTHETIC CANNABINOID COMBINATION THERAPY COMPOSITIONS AND METHODS FOR PERSONALIZED AND TARGETED THERAPIES INCLUDING THE TREATMENT OF INFECTIOUS DISEASES

CROSS-REFERENCE TO RELATED APPLICATIONS

This application claims the benefit of priority to U.S. Provisional Application Ser. No. 63/166,866, filed Mar. 26, 2021, the entire contents of which is hereby incorporated by reference, for all purposes, in its entirety.

FIELD OF TECHNOLOGY

The present disclosure is directed to compositions and methods for personalized and targeted therapeutic treatments, particularly the treatment of pain, inflammation, and infectious diseases in a subject. The present disclosure is also related to combination therapies that including one or more synthetic cannabinoid compounds and at least one active pharmaceutical ingredient. The present disclosure is also related to labeled synthetic cannabinoid therapeutic compositions that include a conjugate of a synthetic cannabinoid compound, a chelator, and a label, that when coupled with imaging may be used to determine in real time optimal dosing and targeting of particular pathways and tissues to provide personalized therapies.

BACKGROUND

Cannabinoids represent a wide range of natural and synthetic compounds whose full-range of therapeutic effects are only beginning to be elucidated. Over 140 different cannabinoids have been isolated from cannabis, each exhibiting various effects. The development of synthetic cannabinoids offers additional therapeutics options for investigation. While there are two known subtypes of cannabinoid receptors, termed $CB_1$ and $CB_2$, there is evidence that additional cannabinoid receptors, e.g., non-$CB_1$ and non-$CB_2$ receptors, may also be present in animals. Further, cannabinoids have also been observed to bind to the G protein-coupled receptor GPR55 in the brain. $CB_1$ receptors are found primarily in the brain, particularly in the basal ganglia and in the limbic system including the hippocampus and the striatum. $CB_2$ receptors are predominantly found in the immune system and the peripheral nervous system. As a result of the differential expression of $CB_1$ and $CB_2$ receptors, and because cannabinoid agonists and antagonists have various binding affinities and selectivities for $CB_1$ and $CB_2$, cannabinoids produce an array of potential therapeutic effects that may be investigated for the treatment of disorders and diseases. There is a need for cannabinoid combination therapy compositions and methods that provide one or more advantages in the treatment of a disease or disorder. Additionally, targeted therapies are needed that target particular pathways and or tissues affected by a disease or disorder.

The diagnosis and treatment of many infectious diseases continues to be poorly understood. In particular, since the COVID-19 outbreak was declared a public health emergency of international concern by the World Health Organization (WHO) on Jan. 30, 2020, the progression of the severe acute respiratory syndrome coronavirus 2 (SARS-COV-2) virus has reminded us of the critical role of an effective host immune response as well as the devastating effect of immune dysregulation. Accordingly, there is a critical need for an efficient approach for both the diagnosis and treatment of infectious diseases, such as COVID-19. However, inconsistencies in the diagnosis and stage identification of infectious diseases and their progression persist making identification of appropriate and efficient treatment protocols challenging. In particular, the diagnosis and prognosis of Cytokine Storm and Cytokine Release Syndrome associated with infectious disease progression has proved difficult. Cytokine Storm and Cytokine Release Syndrome are life-threatening systemic inflammatory syndromes involving elevated levels of circulating cytokines and immune-cell hyperactivation that can be triggered by various therapies, pathogens, autoimmune conditions, and monogenic disorders. Furthermore, effective approaches to tailored or targeted treatment of infectious diseases has also been challenging, including attempts at developing vaccines. Accordingly, there is a need for improved approaches for the treatment of infectious diseases as well was as other diseases and disorders. In particular, there is a need for personalized therapies that are responsive to the genetic, epigenetic, or allelic variations in patients or subjects receiving the therapy. There is also a need for therapies that target particular biological pathways and tissues as well as the monitoring of the targeted delivery of therapeutics in real time in order to provide personalized dosage optimization and treatment decisions.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
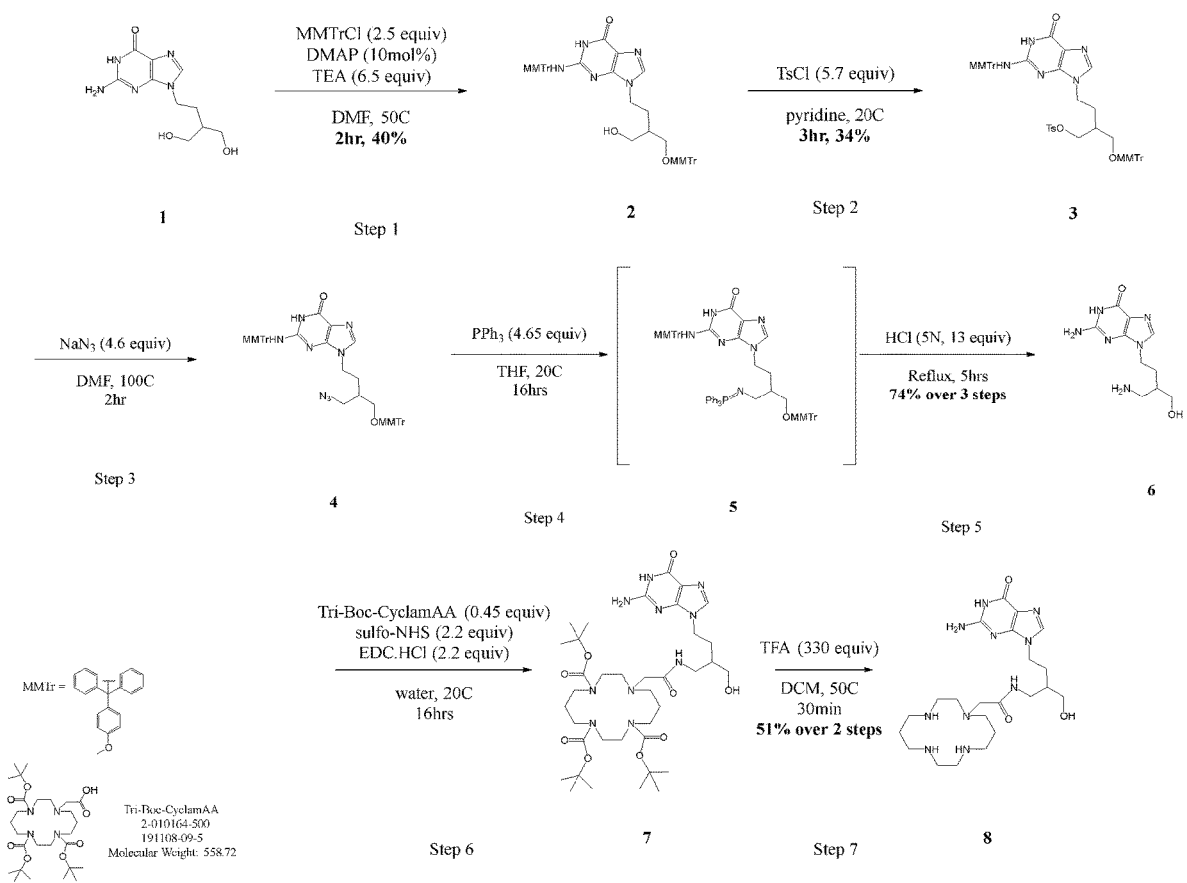
FIG. 1 is exemplary process for the synthesis of the compound according to structural formula I, N-(4-(2-amino-6-oxo-1,6-dihydro-9H-purin-9-yl)-2-(hydroxymethyl)butyl)-2-(1,4,8,11-tetraazacyclotetradecan-1-yl)acetamide, according to an exemplary embodiment of the present disclosure.

It will be appreciated that numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein.

The present disclosure provides combination therapy compositions that includes one or more synthetic cannabinoid compounds and at least one active pharmaceutical ingredient. The one or more synthetic cannabinoid compound may include a cannabinoid receptor agonist or a cannabinoid receptor antagonist. The cannabinoid receptor may be an animal cannabinoid receptor, or a mammalian cannabinoid receptor, or a human cannabinoid receptor. The cannabinoid receptor may be cannabinoid receptor subtype $CB_1$ or cannabinoid receptor subtype $CB_2$. The cannabinoid receptor may also be a non-$CB_1$ and a non-$CB_2$ receptor.

The one or more synthetic cannabinoid compounds may include a synthetic agonist for cannabinoid receptor subtype $CB_1$ and/or a synthetic agonist for cannabinoid receptor subtype $CB_2$. The one or more synthetic cannabinoid compounds may also include a synthetic antagonist for cannabinoid receptor subtype $CB_1$ and/or a synthetic antagonist for cannabinoid receptor subtype $CB_2$. The combination therapy may also include a synthetic cannabinoid compound that is a synthetic selective $CB_1$ agonist and/or a synthetic selective $CB_2$ agonist. For instance, the synthetic antagonist for cannabinoid receptor subtype $CB_1$ may include a diarylopyrazole compound. In other instances, the synthetic antagonist for cannabinoid receptor subtype $CB_1$ may include a compound selected from the group consisting of N-(piperidin-1-yl)-5-(4-chlorophenyl)-1-(2,4-dichlorophenyl)-4-methyl-1H-pyrazole-3-carboxamidehydrochloride (SR141716A or Rimonabant), N-(piperdin-1-yl)-5-(4-iodophenyl)-1-(2,4-dichlorophenyl)-4-methyl-1H-pyrazole-3-carboxyamide (AM251), N-(morpholin-4-yl)-1-(2,4-dichlorophenyl)-5-(4-iodophenyl)-4-methyl-1H-pyrazole-3 carboxamide (AM281), 4-[6-Methoxy-2-(4-methoxyphenyl)benzofuran-3-carbonyl]benzonitrile (LY320135), and any combination thereof.

The one or more synthetic cannabinoid compounds may also include 5-(1,1-Dimethylheptyl)-2-[5-hydroxy-2-(3-hydroxypropyl)cyclohexyl]phenol, also known as CP-55940. In some instances, the one or more synthetic cannabinoid compounds may include (6aR,10aR)-6,6,9-trimethyl-3-pentyl-6a,7,8,10a-tetrahydrobenzo[c]chromen-1-ol, also known as Dronabinol or Marinol. The one or more synthetic cannabinoid compounds may also include (6aR,10aR)-1-hydroxy-6,6-dimethyl-3-(2-methyloctan-2-yl)-7,8,10,10a-tetrahydro-6aH-benzo[c]chromen-9-one, which is also known as Nabilone. The one or more synthetic cannabinoid compounds may also include an aminoalkylindole compound.

The one or more synthetic cannabinoid compounds used in the combination therapy may also include (2-iodo-5-nitrophenyl)-(1-(1-methylpiperidin-2-ylmethyl)-1H-indol-3-yl)methanone, also known as AM1241. 4-[4-(1,1-dimethylheptyl)-2,6-dimethoxyphenyl]-6,6-dimethyl-bicyclo[3.1.1]hept-2-ene-2-methanol, also known as HU-308, may also be included in the one or more synthetic cannabinoid compounds. The one or more synthetic cannabinoid compounds may also include (6aR,10aR)-9-(hydroxymethyl)-6,6-dimethyl-3-(2-methyloctan-2-yl)-6a,7,10,10a-tetrahydrobenzo[c]chromen-1-ol, also known as HU-210.

The one or more synthetic cannabinoid compounds used in the combination therapy may also be selected from the group consisting of a diarylopyrazole, N-(piperidin-1-yl)-5-(4-chlorophenyl)-1-(2,4-dichlorophenyl)-4-methyl-1H-pyrazole-3-carboxamidehydrochloride (SR141716A or Rimonabant), N-(piperdin-1-yl)-5-(4-iodophenyl)-1-(2,4-dichlorophenyl)-4-methyl-1H-pyrazole-3-carboxyamide (AM251), N-(morpholin-4-yl)-1-(2,4-dichlorophenyl)-5-(4-iodophenyl)-4-methyl-1H-pyrazole-3 carboxamide (AM281), 4-[6-Methoxy-2-(4-methoxyphenyl)benzofuran-3-carbonyl]benzonitrile (LY320135), 5-(1,1-Dimethylheptyl)-2-[5-hydroxy-2-(3-hydroxypropyl)cyclohexyl]phenol (CP-55940), (6aR,10aR)-6,6,9-trimethyl-3-pentyl-6a,7,8,10a-tetrahydrobenzo[c]chromen-1-ol (Dronabinol or Marinol), (6aR,10aR)-1-hydroxy-6,6-dimethyl-3-(2-methyloctan-2-yl)-7,8,10,10a-tetrahydro-6aH-benzo[c]chromen-9-one (Nabilone), an aminoalkylindole, (2-iodo-5-nitrophenyl)-(1-(1-methylpiperidin-2-ylmethyl)-1H-indol-3-yl)methanone (AM1241), 4-[4-(1,1-dimethylheptyl)-2,6-dimethoxyphenyl]-6,6-dimethyl-bicyclo[3.1.1]hept-2-ene-2-methanol (HU-308), (6aR,10aR)-9-(hydroxymethyl)-6,6-dimethyl-3-(2-methyloctan-2-yl)-6a,7,10,10a-tetrahydrobenzo[c]chromen-1-ol (HU-210), (2R,4R,4aR,6S,8aS)-6-(1-Hydroxymethmethyl)-4-[2-hydroxy-4-(2-methyl-2-octanyl)phenyl]decahydro-2-naphthalenol (CP55244), 2-[(1S,3R)-3-hydroxycyclohexyl]-5-(2-methyloctan-2-yl)phenol (CP47497), (11R)-2-Methyl-11-[(morpholin-4-yl)methyl]-3-(naphthalene-1-carbonyl)-9-oxa-1-azatricyclo [6.3.1.0]dodeca-2,4(12),5,7-tetraene (R-(+)-WINS 5212), (2-Methyl-1-propyl-1H-indol-3-yl)-1-naphthalenylmethanone (JAVH-015), 1-(2,3-Dichlorobenzoyl)-5-methoxy-2-methyl-3-[2-(4-morpholinyl)ethyl]-1H-indole (L-768242), and any combination thereof.

In some instances, the one or more synthetic cannabinoid compounds may be a synthetic eicosanoid. For example, the one or more synthetic cannabinoid compounds may be selected from the group consisting of methanandamide (R and S isomers), arachidonyl-2-chloroethylamide (ACEA), arachidonylcyclopropylamide (ACPA), and any combination thereof.

The one or more synthetic cannabinoid compounds may also include desacetyl-L-nantradol or 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carboxamide], also known as VYR206 and having a structure according to Formula IV.

The one or more synthetic cannabinoid compounds may also include a synthetic selective $CB_2$ agonist selected from the group consisting of 4-[4-(1,1-dimethylheptyl)-2,6-dimethoxyphenyl]-6,6-dimethyl-bicyclo[3.1.1]hept-2-ene-2-methanol (HU-308), 3-(1,1-Dimethylbutyl)-1-deoxy-$\Delta^8$-tetrahydrocannabinol (JWH-133), JWH-139, 3-(1,1-dimethylheptyl)-6aR,7,10,10aR-tetrahydro-1-methoxy-6,6,9-trimethyl-6H-dibenzo[b,d]pyran (L-759633), (6aR,10aR)-3-(1,1-Dimethylheptyl)-6a,7,8,9,10,10a-hexahydro-1-methoxy-6,6-dimethyl-9-methylene-6H-dibenzo[b,d]pyran (L-759656).

In at least some instances, at least one of the one or more synthetic cannabinoid compounds used in the combination therapy composition is conjugated to a chelator and a label to form a synthetic cannabinoid-chelator-label conjugate. In other cases, at least one of the one or more synthetic cannabinoid compounds is conjugated to a chelator, a label, and a nucleoside analog to form a synthetic cannabinoid-chelator-label-nucleoside analog conjugate.

In such cases, the nucleoside analog may be a guanine analog. In other cases, the nucleoside analog may be a cell replication check point ligand. In some instances, the nucleoside analog may be a synthetic analog. In other instances, the nucleoside analog may be a natural analog. In some cases, the nucleoside analog may be guanine. According to at least one aspect, the nucleoside analog may be selected from the group consisting of adenine, adenosine, deoxyadenosine, guanine, guanosine, dexoyguanosine, thymine, 5-methyluridine, thymidine, uracile, uridine, deoxyuridine, cytosine, cytidine, deoxycytidine, and any combination thereof. The nucleoside analog may, in some instances, be arabinosyl nucleoside.

In some instances, the chelator may be an aminated chelator or an acid chelator. In some instances, the chelator may be a N4 chelator or ligand. The chelator, may be, for example, cyclam, 6-carboxy-1,4,8,11-tetraazaundecane, or 1,4,8,11-tetraazabicyclohexadecane.

The label may be a radionuclide label. In particular, the label may be a radiotherapeutic label capable of delivering a therapeutically effective amount of radiation to a tissue in the subject targeted by the conjugate. In such instances, the radiotherapeutic label may be selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof. In at least some instances, the radionuclide label may be configured to facilitate contrast-enhanced imaging when administered to a mammalian subject in conjunction with diagnostic imaging.

In some instances, the label may be a non-radioactive metal capable of providing an advantageous therapeutic response at a tissue in the subject targeted by the conjugate. In such instances, the non-radioactive metal may be selected from the group consisting of rhenium, platinum, copper, iron, arsenic, lead, tantalum, and any combination thereof. In some instances, the non-radioactive metal may be selected because it is toxic to an infectious agent causing an infection in the subject. In such cases, the advantageous therapeutic response may be toxicity-induced cell death or viral particle inactivation, reduced viral replication, and/or reduced viral load in the tissue.

The conjugate may include a N4-guanine (N4amG) such as cyclam-am-guanine. In some instances, the conjugate may comprise N-(4-(2-amino-6-oxo-1,6,-dihydro-9H-purin-9-yl)-2-(hydroxymethyl)butyl)-2-(1,4,8,11-tetraazacyclotetradecan-1-yl)acetamide, corresponding to a compound characterized by the structure according to Formula I:

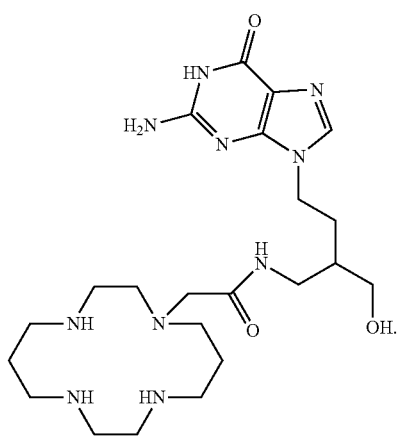

Formula I

In other instances, the conjugate may comprise N-(9-(4-amino-3-(hydroxymethyl)butyl)-6-oxo-6,9-dihydro-1H-purin-2-yl)-2-(1,4,8,11-tetraazacyclotetradecan-1-yl)acetamide, corresponding to a compound characterized by the structure according to Formula II:

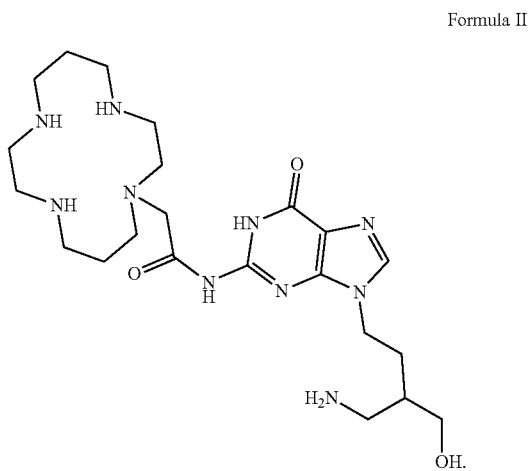 [SMILES: NCC(CO)CCn1cnc2c(=O)[nH]c(NC(=O)CN3CCCNCCNCCCNCC3)nc21]

Formula II

In still other instances, the conjugate may comprise N-(9-(4-(2-(1,4,8,11-tetraazacyclotetradecan-1-yl)acetamido-3-(hydroxymethyl)butyl)-6-oxo-6,9-dihydro-1H-purin-2-yl)-2-(1,4,8,11-tetraazacyclotetradecan-1-yl)acetamide, corresponding to a compound characterized by the structure according to Formula III:

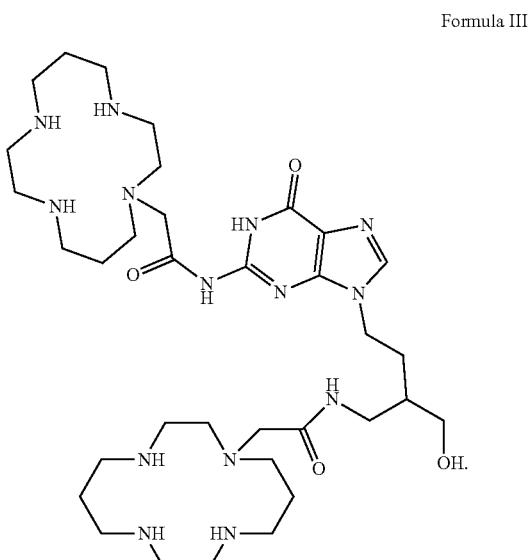

Formula III

In still other instances, the conjugate may comprise 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carboxamide], corresponding to a compound characterized by the structure according to Formula IV:

Formula IV

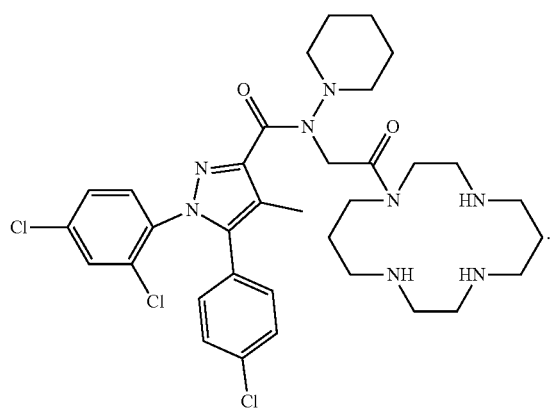

Any of the conjugates disclosed herein, such as the conjugates according to Formula I, Formula II, Formula III, Formula IV, may further be labeled with a radionuclide label to form the compositions comprising a conjugate of a nucleoside analog, a chelator, and a label. For example, the conjugates in Formulas I-IV may include a label selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof.

The presently disclosed combination therapy compositions may also include one or more natural cannabinoid compounds. The one or more natural cannabinoid compounds may be selected from endocannabinoids and phytogenic cannabinoids. The one or more natural cannabinoid compounds may also be selected from the group of cannabinoid compounds obtained from the *Cannabis sativa* or *Cannabis indica* medical marijuana strains. The one or more natural cannabinoid compounds may also include a flavonoid and/or a terpenoid. The one or more natural cannabinoid compounds may also include a phytogenic cannabinoid selected from the group consisting of flavonoids, terpenoids, Nabiximols, Cannador, cannabidiol (CBD), cannabinol (CBN), cannabigerol, tetrahydrocannabivarin, cannabichromene, $\Delta^8$-THC, $\Delta^9$-tetrahydrocannabinol ($\Delta^9$-THC), and any combination thereof. The one or more natural cannabinoid compounds may also include a compound selected from the group consisting of Nabiximols, Cannador, cannabidiol (CBD), cannabinol (CBN), cannabigerol, tetrahydrocannabivarin, cannabichromene, $\Delta^8$-THC, $\Delta^9$-tetrahydrocannabinol ($\Delta^9$-THC), and any combination thereof. The one or more natural cannabinoid compounds may also include an endocannabinoid compound selected from the group consisting of N-arachidonoylethanolamine, (AEA) or anandamide, 2-arachidonoylglycerol (2-AG), noladin ether, virodhamine, N-arachidonylodopamine (NADA), and any combination thereof.

The at least one active pharmaceutical ingredient may be any active pharmaceutical ingredient effective in the treatment of infectious diseases, pain, inflammation, cardiovascular disease, neurological disorders, psychiatric disorders, immunological disorders, endocrine disorders, and proliferative and neoplastic disorders. In at least some instances, the active pharmaceutical ingredient is an analgesic. In such instances, the analgesic may be selected from the group consisting of nonsteroidal anti-inflammatory drugs (NSAIDs), aspirin, ibuprofen, acetaminophen, naproxen, codeine, salicylates, narcotic analgesics, cyclooxygenase-2 (cox-2) inhibitors, calcitonin gene-related peptide (CGRP) inhibitors, opioids, ziconotide, hydrocodone, oxycodone, fentanyl, morphine, oxymorphone, buprenorphine, levorphanol, tramadol, hydromorphone, methadone, meperidine, propoxyphene, nalbuphine, and any combination thereof.

The active pharmaceutical ingredient may also be an anti-inflammatory compound. In such instances, the anti-inflammatory compound may be selected from the group consisting of nonsteroidal anti-inflammatory drugs (NSAIDs), aspirin, ibuprofen, naproxen, corticosteroids, cyclooxygenase-2 (cox-2) inhibitors, salicylates, diclofenac, diflunisal, etodolac, celecoxib, etoricoxib, famotidine, flurbiprofen, indomethacin, ketoprofen, mefenamic acid, meloxicam, nabumetone, oxaprozin, piroxicam, sulindac, glucocorticoids, prednisone, cortisone, hydrocortisone, bethamethasone, prednisolone, triamcinolone, methylprednisolone, dexamethasone, ethamethasoneb, and any combination thereof.

The active pharmaceutical ingredient may also be an antiviral compound. In such instances, the antiviral compound may be selected from the group consisting of remdesivir, oseltamivir phosphate, zanamivir, peramivir, baloxavir marboxil, darunavir, atazanavir, ritonavir, acyclovir, valacyclovir, valganciclovir, tenofovir, raltegravir, viral attachment inhibitors, viral entry inhibitors, uncoating inhibitors, protease inhibitors, polymerase inhibitors, nucleoside and nucleotide reverse transcriptase inhibitors, nonnucleoside reverse-transcriptase inhibitors, integrase inhibitors, and any combination thereof.

According to one aspect of the present disclosure, the presently disclosed combination therapy compositions produce at least one synergistic therapeutic effect when administered to a subject. The at least one synergistic therapeutic effect may be selected, for example, from the group consisting of reduced observed toxicity of the at least one active pharmaceutical ingredient, reduction in the administration dosage or amount of active pharmaceutical ingredient required to obtain an advantageous clinical outcome, improved clinical outcomes of the combination therapy as compared to the separate administration of the one or more synthetic cannabinoid compounds or the at least one active pharmaceutical ingredient, and any combination thereof.

According to another aspect of the present disclosure, a method of treating or alleviating pain in a subject in need thereof is provided. The method may include administering to the subject a pharmaceutically effective amount of one of the presently disclosed combination therapy compositions. In at least some instances, the method of treating or alleviating pain includes administering to the subject a combination therapy composition that includes an analgesic as the active pharmaceutical ingredient.

According to another aspect of the present disclosure, a method of treating inflammation in a subject in need thereof is provided. The method may include administering to the subject a pharmaceutically effective amount of any of the presently disclosed combination therapy compositions. In at least some instances, the method of treating inflammation includes administering to the subject a combination therapy composition that includes an anti-inflammatory as the active pharmaceutical ingredient.

According to another aspect of the present disclosure, a method of treating an infectious disease in a subject in need thereof is provided. The method may include administering to the subject a pharmaceutically effective amount of any of the presently disclosed combination therapy compositions. The method may also include administering to the subject a therapeutically effective amount of a radiotherapeutic regimen. The radiotherapeutic regimen delivers radiation to an infected tissue in the subject in need of treatment. The radiotherapeutic regimen may cause increased viral particle inactivation, reduced viral replication, and/or reduced viral load in the tissue. The radiotherapeutic regimen may include administration of a radioactive agent selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof. The at least one active pharmaceutical ingredient in the combination therapy may include one or more antiviral compounds. For example, the one or more antiviral compounds may be selected from the group consisting of remdesivir, oseltamivir phosphate, zanamivir, peramivir, baloxavir marboxil, darunavir, atazanavir, ritonavir, acyclovir, valacyclovir, valganciclovir, tenofovir, raltegravir, viral attachment inhibitors, viral entry inhibitors, uncoating inhibitors, protease inhibitors, polymerase inhibitors, nucleoside and nucleotide reverse transcriptase inhibitors, nonnucleoside reverse-transcriptase inhibitors, integrase inhibitors, and any combination thereof.

According to another aspect of the present disclosure, a method of treating an infectious disease in a subject in need thereof is provided. The method may include administering to the subject a pharmaceutically effective amount of any of the presently disclosed combination therapy compositions. In at least some instances, the method of treating an infectious disease includes administering to the subject a combination therapy composition that includes an antiviral as the active pharmaceutical ingredient. In at least some instances, the label provides an advantageous therapeutic effect in treating the infectious disease. In some instances, the label is a radiotherapeutic label capable of delivering radiation to an infected tissue in the subject and the advantageous therapeutic effect is increased viral particle inactivation, reduced viral replication, and/or reduced viral load in the tissue. The radiotherapeutic label may be, for example, Technetium-99, Gallium-68, Copper-60, Copper-64, Indium-111, Holmium-166, Rhenium-186, Rhenium-188, Yttrium-90, Lutetium-177, Radium-223, Actinium-225, or any combination thereof. In other instances, the label is a non-radioactive metal that is toxic to an infectious diseases causing agent and the advantageous therapeutic effect is toxicity-induced cell death or viral particle inactivation, reduced viral replication, and/or reduced viral load in the tissue. In such instances, the non-radioactive metal is selected from the group consisting of rhenium, platinum, copper, iron, arsenic, lead, tantalum, and any combination thereof.

In at least some instances, the infectious disease is a viral infection. For instance, the infectious disease may be a respiratory viral infection selected from the group consisting of human influenza, the common cold, Middle East respiratory syndrome (MERS), severe acute respiratory syndrome coronavirus (SARS), and COVID-19. The infectious disease may also be caused by infection by a virus selected from the group consisting of severe acute respiratory syndrome coronavirus (SARS-CoV), severe acute respiratory syndrome coronavirus 2 (SARS-CoV-2), Middle East respiratory syndrome-related coronavirus (MERS-CoV), human coronavirus NL63 (HCoV NL63), human coronavirus OC43 (HCoV-OC43), human coronavirus HKU1 (HCoV HKU1), and human coronavirus 229E (HCoV-229E).

According to another aspect of the present disclosure, a method of treating a condition in a subject in need thereof is provided. The method may include administering to the subject a pharmaceutically effective amount of any of the presently disclosed combination therapy compositions. The condition treated may be, for example, cardiovascular disease, neurological disorders, psychiatric disorders, immunological disorders, endocrine disorders, and proliferative and neoplastic disorders.

The presently disclosed methods of administering a combination therapy composition to a subject in need may further include performing an imaging technique on the subject or a portion thereof. The imaging technique may be capable of detecting one or more signals from the combination therapy composition to generate one or more data images. For example, the imaging technique may be positron emission tomography (PET), computed tomography (CT), single photon emission computed tomography (SPECT), magnetic resonance imaging (MM), near-infrared (NIR), optical imaging, optoacoustic imaging, or ultrasound.

The presently disclosed methods of administering a combination therapy composition to a subject in need may further include making at least one treatment decision based on the one or more data images. The treatment decision may include, for example, raising or lowering the dose of combination therapy composition administered to the subject, determining the optimal dosage of administration for the particular subject based on the one or more data images, determining whether a dysfunctional pathway or tissue of interest associated with a disease was successfully targeted by the combination therapy composition, and/or determining if an adverse advent was caused by administration of the combination therapy composition.

The presently disclosed methods of administering a combination therapy composition to a subject in need may further include monitoring the uptake of one or more components of the combination therapy composition based on the one or more data images. In such instances, the one or more data images may provide for visual assessment of uptake at a tissue site of interest of one or more components of the combination therapy composition.

According to another aspect of the present disclosure, a method of administering a personalized and targeted combination therapy to a subject in need thereof is provided. The method may include administering to the subject a pharmaceutically effective amount of any of the presently disclosed labeled combination therapy compositions. The method may also include performing an imaging technique on the subject or a portion thereof, wherein the imaging technique is capable of detecting one or more signals from the labeled combination therapy composition to generate one or more data images. The method may also include making at least one personalized treatment decision based on the one or more data images. For example, the treatment decision may include raising or lowering the dose of combination therapy composition administered to the subject, determining the optimal dosage of administration for the particular subject based on the one or more data images, determining whether a dysfunctional pathway or tissue of interest associated with a disease was successfully targeted by the combination therapy composition, and/or determining if an adverse advent was caused by administration of the combination therapy composition.

The pharmaceutically effective amount of combination therapy composition administered in the presently disclosed methods of administering a combination therapy composition, may be from about 0.1 mg/kg to about 1000 mg/kg of body weight per day, or from about 0.1 mg/kg to about 750 mg/kg of body weight per day, or from about 0.1 mg/kg to about 500 mg/kg of body weight per day, or from about 0.1 mg/kg to about 250 mg/kg of body weight per day, or from about 0.1 mg/kg to about 100 mg/kg of body weight per day, or from about 0.1 mg/kg to about 75 mg/kg of body weight per day, or from about 0.1 mg/kg to about 50 mg/kg of body weight per day, or from about 0.1 mg/kg to about 30 mg/kg of body weight per day, or from about 0.1 mg/kg to about 10 mg/kg of body weight per day, or from about 0.1 mg/kg to about 5 mg/kg of body weight per day, or from about 25 mg/kg to about 100 mg/kg of body weight per day, or from about 50 mg/kg to about 100 mg/kg of body weight per day, or from about 100 mg/kg to about 500 mg/kg of body weight per day, or from about 25 mg/kg to about 150 mg/kg of body weight per day, or from about 50 mg/kg to about 200 mg/kg of body weight per day.

The pharmaceutically effective amount of the combination therapy composition may be administered once daily, or twice daily (b.i.d.), or three times daily (t.i.d.), or four times daily (q.i.d.). The combination therapy composition may be administered by any administration route, including but not limited to, oral, intravenous, sublingual, buccal, rectal, intranasal, parenteral, enteral, transdermal, intramuscular, and any combination thereof.

According to another aspect of the present disclosure, labeled synthetic cannabinoid therapeutic compositions are provided. The labeled synthetic cannabinoid therapeutic compositions may include a conjugate of a synthetic cannabinoid compound, a chelator, and a label. The presently disclosed labeled synthetic cannabinoid therapeutic compositions are capable of providing targeted and personalized therapies when coupled with an imaging technique capable of detecting the label conjugated to the synthetic cannabinoid therapeutic compound. In particular, the presently disclosed labeled synthetic cannabinoid therapeutic compositions may provide real time optimal dosing determination and visual and quantitative assessment of the targeting of specific biological tissues and pathways.

The synthetic cannabinoid compound used in the labeled synthetic cannabinoid therapeutic compositions may include a cannabinoid receptor agonist or a cannabinoid receptor antagonist. The cannabinoid receptor may be an animal cannabinoid receptor, or a mammalian cannabinoid receptor, or a human cannabinoid receptor. The cannabinoid receptor may be cannabinoid receptor subtype $CB_1$ or cannabinoid receptor subtype $CB_2$. The cannabinoid receptor may also be a non-$CB_1$ and a non-$CB_2$ receptor.

The synthetic cannabinoid compounds used in the labeled synthetic cannabinoid therapeutic compositions may also include a synthetic agonist for cannabinoid receptor subtype $CB_1$ and/or a synthetic agonist for cannabinoid receptor subtype $CB_2$. The synthetic cannabinoid compound may also include a synthetic antagonist for cannabinoid receptor subtype $CB_1$ and/or a synthetic antagonist for cannabinoid receptor subtype $CB_2$. The labeled synthetic cannabinoid therapeutic compositions may also include a synthetic cannabinoid compound that is a synthetic selective $CB_1$ agonist and/or a synthetic selective $CB_2$ agonist. For instance, the synthetic antagonist for cannabinoid receptor subtype $CB_1$ may include a diarylopyrazole compound. In other instances, the synthetic antagonist for cannabinoid receptor subtype $CB_1$ may include a compound selected from the group consisting of N-(piperidin-1-yl)-5-(4-chlorophenyl)-1-(2,4-dichlorophenyl)-4-methyl-1H-pyrazole-3-carboxamidehydrochloride (SR141716A or Rimonabant), N-(piperdin-1-yl)-5-(4-iodophenyl)-1-(2,4-dichlorophenyl)-4-methyl-1H-pyrazole-3-carboxyamide (AM251), N-(morpholin-4-yl)-1-(2,4-dichlorophenyl)-5-(4-iodophenyl)-4-methyl-1H-pyrazole-3 carboxamide (AM281), 4-[6-Methoxy-2-(4-methoxyphenyl)benzofuran-3-carbonyl]benzonitrile (LY320135), and any combination thereof.

The synthetic cannabinoid compounds used in the labeled synthetic cannabinoid therapeutic compositions may also include 5-(1,1-Dimethylheptyl)-2-[5-hydroxy-2-(3-hydroxypropyl)cyclohexyl]phenol, also known as CP-55940. In some instances, the synthetic cannabinoid compounds may include (6aR,10aR)-6,6,9-trimethyl-3-pentyl-6a,7,8,10a-tetrahydrobenzo[c]chromen-1-ol, also known as Dronabinol or Marinol. The synthetic cannabinoid compounds may also include (6aR,10aR)-1-hydroxy-6,6-dimethyl-3-(2-methyloctan-2-yl)-7,8,10,10a-tetrahydro-6aH-benzo[c]chromen-9-one, which is also known as Nabilone. The synthetic cannabinoid compounds may also include an aminoalkylindole compound.

The synthetic cannabinoid compounds used in the labeled synthetic cannabinoid therapeutic compositions may also include (2-iodo-5-nitrophenyl)-(1-(1-methylpiperidin-2-ylmethyl)-1H-indol-3-yl)methanone, also known as AM1241. 4-[4-(1,1-dimethylheptyl)-2,6-dimethoxyphenyl]-6,6-dimethyl-bicyclo[3.1.1]hept-2-ene-2-methanol, also known as HU-308, may also be included as a synthetic cannabinoid compound. The synthetic cannabinoid compound may also include (6aR,10aR)-9-(hydroxymethyl)-6,6-dimethyl-3-(2-methyloctan-2-yl)-6a,7,10,10a-tetrahydrobenzo[c]chromen-1-ol, also known as HU-210.

The synthetic cannabinoid compounds used in the labeled synthetic cannabinoid therapeutic compositions may also be selected from the group consisting of a diarylopyrazole, N-(piperidin-1-yl)-5-(4-chlorophenyl)-1-(2,4-dichlorophenyl)-4-methyl-1H-pyrazole-3-carboxamidehydrochloride (SR141716A or Rimonabant), N-(piperdin-1-yl)-5-(4-iodophenyl)-1-(2,4-dichlorophenyl)-4-methyl-1H-pyrazole-3-carboxyamide (AM251), N-(morpholin-4-yl)-1-(2,4-dichlorophenyl)-5-(4-iodophenyl)-4-methyl-1H-pyrazole-3carboxamide (AM281), 4-[6-Methoxy-2-(4-methoxyphenyl)benzofuran-3-carbonyl]benzonitrile (LY320135), 5-(1,1-Dimethylheptyl)-2-[5-hydroxy-2-(3-hydroxypropyl)cyclohexyl]phenol (CP-55940), (6aR, 10aR)-6,6,9-trimethyl-3-pentyl-6a,7,8,10a-tetrahydrobenzo[c]chromen-1-ol (Dronabinol or Marinol), (6aR,10aR)-1-hydroxy-6,6-dimethyl-3-(2-methyloctan-2-yl)-7,8,10,10a-tetrahydro-6aH-benzo[c]chromen-9-one (Nabilone), an aminoalkylindole, (2-iodo-5-nitrophenyl)-(1-(1-methylpiperidin-2-ylmethyl)-1H-indol-3-yl)methanone (AM1241), 4-[4-(1,1-dimethylheptyl)-2,6-dimethoxyphenyl]-6,6-dimethyl-bicyclo[3.1.1]hept-2-ene-2-methanol (HU-308), (6aR, 10aR)-9-(hydroxymethyl)-6,6-dimethyl-3-(2-methyloctan-2-yl)-6a,7,10,10a-tetrahydrobenzo[c]chromen-1-ol (HU-210), (2R,4R,4aR,6S,8aS)-6-(Hydroxymethyl)-4-[2-hydroxy-4-(2-methyl-2-octanyl)phenyl]decahydro-2-naphthalenol (CP55244), 2-[(1S,3R)-3-hydroxycyclohexyl]-5-(2-methyloctan-2-yl)phenol (CP47497), (11R)-2-Methyl-11-[(morpholin-4-yl)methyl]-3-(naphthalene-1-carbonyl)-9-oxa-1-azatricyclo[6.3.1.0]dodeca-2,4(12), 5,7-tetraene (R-(+)-WIN55212), (2-Methyl-1-propyl-1H-indol-3-yl)-1-naphthalenylmethanone (JWH-015), 142,3-Dichlorobenzoyl)-5-methoxy-2-methyl-3-[2-(4-morpholinyl)ethyl]-1H-indole (L-768242), and any combination thereof.

In some instances, the synthetic cannabinoid compound used in the labeled synthetic cannabinoid therapeutic compositions may be a synthetic eicosanoid. For example, the synthetic cannabinoid compounds may be selected from the group consisting of methanandamide (R and S isomers), arachidonyl-2-chloroethylamide (ACEA), arachidonylcyclopropylamide (ACPA), and any combination thereof.

The synthetic cannabinoid compound used in the labeled synthetic cannabinoid therapeutic compositions may also include desacetyl-L-nantradol or 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carboxamide], also known as VYR206 and having a structure according to Formula IV.

The synthetic cannabinoid compounds used in the labeled synthetic cannabinoid therapeutic compositions may also include a synthetic selective $CB_2$ agonist selected from the group consisting of 4-[4-(1,1-dimethylheptyl)-2,6-dimethoxyphenyl]-6,6-dimethyl-bicyclo[3.1.1]hept-2-ene-2-methanol (HU-308), 3-(1,1-Dimethylbutyl)-1-deoxy-$\Delta^8$-tetrahydrocannabinol (JWH-133), JWH-139, 3-(1,1-dimethylheptyl)-6aR,7,10,10aR-tetrahydro-1-methoxy-6,6, 9-trim ethyl-6H-dibenzo[b,d]pyran (L-759633), (6aR, 10aR)-3-(1,1-Dimethylheptyl)-6a,7,8,9,10,10a-hexahydro-1-m ethoxy-6,6-dimethyl-9-methyl ene-6H-dibenzo[b,d] pyran (L-759656).

In at least some instances, the synthetic cannabinoid compound used in the labeled synthetic cannabinoid therapeutic compositions is further conjugated to a nucleoside analog to form a synthetic cannabinoid-chelator-label-nucleoside analog conjugate. In such cases, the nucleoside analog may be a guanine analog. In other cases, the nucleoside analog may be a cell replication check point ligand. In some instances, the nucleoside analog may be a synthetic analog. In other instances, the nucleoside analog may be a natural analog. In some cases, the nucleoside analog may be guanine. According to at least one aspect, the nucleoside analog may be selected from the group consisting of adenine, adenosine, deoxyadenosine, guanine, guanosine, dexoyguanosine, thymine, 5-methyluridine, thymidine, uracile, uridine, deoxyuridine, cytosine, cytidine, deoxycytidine, and any combination thereof. The nucleoside analog may, in some instances, be arabinosyl nucleoside.

In some instances, the chelator may be an aminated chelator or an acid chelator. In some instances, the chelator may be a N4 chelator or ligand. The chelator, may be, for example, cyclam, 6-carboxy-1,4,8,11-tetraazaundecane, or 1,4,8,11-tetraazabicyclohexadecane.

The label may be a radionuclide label. In particular, the label may be a radiotherapeutic label capable of delivering a therapeutically effective amount of radiation to a tissue in the subject targeted by the conjugate. In such instances, the radiotherapeutic label may be selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof. In at least some instances, the radionuclide label may be configured to facilitate contrast-enhanced imaging when administered to a mammalian subject in conjunction with diagnostic imaging.

In some instances, the label may be a non-radioactive metal capable of providing an advantageous therapeutic response at a tissue in the subject targeted by the conjugate. In such instances, the non-radioactive metal may be selected from the group consisting of rhenium, platinum, copper, iron, arsenic, lead, tantalum, and any combination thereof. In some instances, the non-radioactive metal may be selected because it is toxic to an infectious agent causing an infection in the subject. In such cases, the advantageous therapeutic response may be toxicity-induced cell death or viral particle inactivation, reduced viral replication, and/or reduced viral load in the tissue.

The conjugate may include a N4-guanine (N4amG) such as cyclam-am-guanine. In some instances, the conjugate may comprise N-(4-(2-amino-6-oxo-1,6,-dihydro-9H-purin-9-yl)-2-(hydroxymethyl)butyl)-2-(1,4,8,11-tetraazacyclotetradecan-1-yl)acetamide, corresponding to a compound characterized by the structure according to Formula I. In other instances, the conjugate may comprise N-(9-(4-amino-3-(hydroxymethyl)butyl)-6-oxo-6,9-dihydro-1H-purin-2-yl)-2-(1,4,8,11-tetraazacyclotetradecan-1-yl)acetamide, corresponding to a compound characterized by the structure according to Formula II. In still other instances, the conjugate may comprise N-(9-(4-(2-(1,4,8,11-tetraazacyclotetradecan-1-yl)acetamido-3-(hydroxymethyl)butyl)-6-oxo-6,9-dihydro-1H-purin-2-yl)-2-(1,4,8,11-tetraazacyclotetradecan-1-yl)acetamide, corresponding to a compound characterized by the structure according to Formula III. In still other instances, the conjugate may comprise 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carboxamide], corresponding to a compound characterized by the structure according to Formula IV.

Any of the conjugates disclosed herein, such as the conjugates according to Formula I, Formula II, Formula III, Formula IV, may further be labeled with a radionuclide label to form the compositions comprising a conjugate of a nucleoside analog, a chelator, and a label. For example, the conjugates in Formulas I-IV may include a label selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof.

The presently disclosed labeled synthetic cannabinoid therapeutic compositions may also include one or more natural cannabinoid compounds. The one or more natural cannabinoid compounds may be selected from endocannabinoids and phytogenic cannabinoids. The one or more natural cannabinoid compounds may also be selected from the group of cannabinoid compounds obtained from the *Cannabis sativa* or *Cannabis indica* medical marijuana strains. The one or more natural cannabinoid compounds may also include a flavonoid and/or a terpenoid. The one or more natural cannabinoid compounds may also include a phytogenic cannabinoid selected from the group consisting of flavonoids, terpenoids, Nabiximols, Cannador, cannabidiol (CBD), cannabinol (CBN), cannabigerol, tetrahydrocannabivarin, cannabichromene, $\Delta^8$-THC, $\Delta^9$-tetrahydrocannabinol ($\Delta^9$-THC), and any combination thereof. The one or more natural cannabinoid compounds may also include a compound selected from the group consisting of Nabiximols, Cannador, cannabidiol (CBD), cannabinol (CBN), cannabigerol, tetrahydrocannabivarin, cannabichromene, $\Delta^8$-THC, $\Delta^9$-tetrahydrocannabinol ($\Delta^9$-THC), and any combination thereof. The one or more natural cannabinoid compounds may also include an endocannabinoid compound selected from the group consisting of N-arachidonoylethanolamine, (AEA) or anandamide, 2-arachidonoylglycerol (2-AG), noladin ether, virodhamine, N-arachidonylodopamine (NADA), and any combination thereof.

According to another aspect of the present disclosure, a method of treating or alleviating pain in a subject in need thereof is provided. The method may include administering to the subject a pharmaceutically effective amount of one of the presently disclosed labeled synthetic cannabinoid therapeutic compositions.

According to another aspect of the present disclosure, a method of treating inflammation in a subject in need thereof is provided. The method may include administering to the subject a pharmaceutically effective amount of any of the presently disclosed labeled synthetic cannabinoid therapeutic compositions.

According to another aspect of the present disclosure, a method of treating an infectious disease in a subject in need thereof is provided. The method may include administering to the subject a pharmaceutically effective amount of any of the presently disclosed labeled synthetic cannabinoid therapeutic compositions. In at least some instances, the label provides an advantageous therapeutic effect in treating the infectious disease. In some instances, the the label is a radiotherapeutic label capable of delivering radiation to an infected tissue in the subject and the advantageous therapeutic effect is increased viral particle inactivation, reduced viral replication, and/or reduced viral load in the tissue. The radiotherapeutic label may be, for example, Technetium-99, Gallium-68, Copper-60, Copper-64, Indium-111, Holmium-166, Rhenium-186, Rhenium-188, Yttrium-90, Lutetium-177, Radium-223, Actinium-225, or any combination thereof. In other instances, the label is a non-radioactive metal that is toxic to an infectious diseases causing agent and the advantageous therapeutic effect is toxicity-induced cell death or viral particle inactivation, reduced viral replication, and/or reduced viral load in the tissue. In such instances, the non-radioactive metal is selected from the group consisting of rhenium, platinum, copper, iron, arsenic, lead, tantalum, and any combination thereof.

In at least some instances, the infectious disease is a viral infection. For instance, the infectious disease may be a respiratory viral infection selected from the group consisting of human influenza, the common cold, Middle East respiratory syndrome (MERS), severe acute respiratory syndrome coronavirus (SARS), and COVID-19. The infectious disease may also be caused by infection by a virus selected from the group consisting of severe acute respiratory syndrome coronavirus (SARS-CoV), severe acute respiratory syndrome coronavirus 2 (SARS-CoV-2), Middle East respiratory syndrome-related coronavirus (MERS-CoV), human coronavirus NL63 (HCoV NL63), human coronavirus OC43 (HCoV-OC43), human coronavirus HKU1 (HCoV HKU1), and human coronavirus 229E (HCoV-229E).

According to another aspect of the present disclosure, a method of treating a condition in a subject in need thereof is provided. The method may include administering to the subject a pharmaceutically effective amount of any of the presently disclosed labeled synthetic cannabinoid therapeutic compositions. The condition treated may be, for example, cardiovascular disease, neurological disorders, psychiatric disorders, immunological disorders, endocrine disorders, and proliferative and neoplastic disorders.

The presently disclosed methods of administering a labeled synthetic cannabinoid therapeutic compositions to a subject in need may further include performing an imaging technique on the subject or a portion thereof. The imaging technique may be capable of detecting one or more signals from the combination therapy composition to generate one or more data images. For example, the imaging technique may be positron emission tomography (PET), computed tomography (CT), single photon emission computed tomography (SPECT), magnetic resonance imaging (MM), near-infrared (NIR), optical imaging, optoacoustic imaging, or ultrasound.

The presently disclosed methods of administering a labeled synthetic cannabinoid therapeutic compositions to a subject in need may further include making at least one treatment decision based on the one or more data images. The treatment decision may include, for example, raising or lowering the dose of combination therapy composition administered to the subject, determining the optimal dosage of administration for the particular subject based on the one or more data images, determining whether a dysfunctional pathway or tissue of interest associated with a disease was successfully targeted by the combination therapy composition, and/or determining if an adverse advent was caused by administration of the combination therapy composition.

The presently disclosed methods of administering a labeled synthetic cannabinoid therapeutic composition to a subject in need may further include monitoring the uptake of one or more components of the combination therapy composition based on the one or more data images. In such instances, the one or more data images may provide for visual assessment of uptake at a tissue site of interest of one or more components of the labeled synthetic cannabinoid therapeutic compositions.

According to another aspect of the present disclosure, a method of administering a personalized and targeted combination therapy to a subject in need thereof is provided. The method may include administering to the subject a pharmaceutically effective amount of any of the presently disclosed labeled synthetic cannabinoid therapeutic compositions. The method may also include performing an imaging technique on the subject or a portion thereof, wherein the imaging technique is capable of detecting one or more signals from the labeled synthetic cannabinoid therapeutic composition to generate one or more data images. The method may also include making at least one personalized treatment decision based on the one or more data images. For example, the treatment decision may include raising or lowering the dose of combination therapy composition administered to the subject, determining the optimal dosage of administration for the particular subject based on the one or more data images, determining whether a dysfunctional pathway or tissue of interest associated with a disease was successfully targeted by the combination therapy composition, and/or determining if an adverse advent was caused by administration of the combination therapy composition.

The pharmaceutically effective amount of combination therapy composition administered in the presently disclosed methods of administering a labeled synthetic cannabinoid therapeutic composition, may be from about 0.1 mg/kg to about 1000 mg/kg of body weight per day, or from about 0.1 mg/kg to about 750 mg/kg of body weight per day, or from about 0.1 mg/kg to about 500 mg/kg of body weight per day, or from about 0.1 mg/kg to about 250 mg/kg of body weight per day, or from about 0.1 mg/kg to about 100 mg/kg of body weight per day, or from about 0.1 mg/kg to about 75 mg/kg of body weight per day, or from about 0.1 mg/kg to about 50 mg/kg of body weight per day, or from about 0.1 mg/kg to about 30 mg/kg of body weight per day, or from about 0.1 mg/kg to about 10 mg/kg of body weight per day, or from about 0.1 mg/kg to about 5 mg/kg of body weight per day, or from about 25 mg/kg to about 100 mg/kg of body weight per day, or from about 50 mg/kg to about 100 mg/kg of body weight per day, or from about 100 mg/kg to about 500 mg/kg of body weight per day, or from about 25 mg/kg to about 150 mg/kg of body weight per day, or from about 50 mg/kg to about 200 mg/kg of body weight per day.

The pharmaceutically effective amount of the labeled synthetic cannabinoid therapeutic composition may be administered once daily, or twice daily (b.i.d.), or three times daily (t.i.d.), or four times daily (q.i.d.). The labeled synthetic cannabinoid therapeutic composition may be administered by any administration route, including but not limited to, oral, intravenous, sublingual, buccal, rectal, intranasal, parenteral, enteral, transdermal, intramuscular, and any combination thereof.

As used herein, the term "conjugate," in all its forms, refers to a compound formed by the joining of two or more chemical compounds. The term "pharmaceutically acceptable derivative," as used herein, refers to and includes any pharmaceutically acceptable salt, pro-drug, metabolite, ester, ether, hydrate, polymorph, solvate, complex, and adduct of a compound described herein, which, upon administration to a subject, is capable of providing (directly or indirectly) the active ingredient. For example, the term "a pharmaceutically acceptable derivative" of compounds described herein includes all derivatives of the compounds described herein (such as salts, pro-drugs, metabolites, esters, ethers, hydrates, polymorphs, solvates, complexes, and adducts) which, upon administration to a subject, are capable of providing (directly or indirectly) the compounds described herein. As used herein, the term "pharmaceutically acceptable salt" refers to those salts, which retain the biological effectiveness and properties of the parent compound. Unless otherwise indicated, a pharmaceutically acceptable salt includes salts of acidic or basic groups, which may be present in the compounds of the formulae disclosed herein. The present disclosure also provides certain processes, as examples, for the preparation of the above pharmaceutically acceptable salts, their derivatives, their analogs, their tautomeric forms, their stereoisomers, their polymorphs, and pharmaceutical compositions containing them.

Certain embodiments of the present disclosure relate to pharmaceutically acceptable salts formed by the compounds described herein, or their derivatives, their analogs, their tautomeric forms, their stereoisomers, their polymorphs and pharmaceutically acceptable compositions containing them. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenylsubstituted alkanoic acids, hydroxyalkanoic and hydroxyalkandioic acids, aromatic acids, aliphatic and aromatic sulfonic acids, may also be used. Such pharmaceutically acceptable salts thus include acetate, phenyl acetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, beta-hydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydro genphosphate, dihydrogenphosphate, metaphosphate, pyrophosphate, propionate, phenylpropionate, salicylate, succinate, sulfate, bisulfate, pyrosulfate, sulfite, bisulfite, sulfonate, benzenesulfonate, p-bromophenyl sulfonate, chlorobenzenesulfonate, ethane sulfonate, 2-hydroxy ethanesulfonate, methanesulfonate, naphthalene-1-sulfonate, naphthalene-2-sulfonate, p-toluenesulfonate, xylenesulfonate, tartarate, and the like.

It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

The following descriptions of methods, compositions, and results obtained using them are provided merely as illustrative examples. Descriptions of the methods are not intended to require or imply that the steps of the various embodiments must be performed in the order presented. The steps in the foregoing embodiments may be performed in any order. Words such as "then" are not intended to limit the order of the steps; these words are simply used to guide the reader through the description of the methods. Many of the operations may be performed in parallel or concurrently. In addition, the order of the operations may be re-arranged. Various modifications to these embodiments will be readily apparent based on the description provided here, and the generic principles defined here may be applied to other embodiments without departing from the scope of the disclosure.

Further modifications and alternative embodiments of various aspects of the compositions and methods disclosed here will be apparent in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent after having the benefit of this description of the embodiments. Changes may be made in the elements described here without departing from the scope of the embodiments as described in the following claims.

EXAMPLES

Example 1—Synthesis of the Compound According to Formula I, N-(4-(2-amino-6-oxo-1,6,-dihydro-9H-purin-9-yl)-2-(hydroxymethyl)butyl)-2-(1,4,8,11-tetraazacyclotetradecan-1-yl)acetamide The guanine nucleoside analog compound according to Formula I,

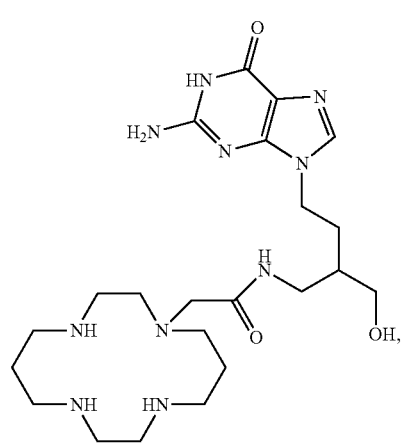

Formula I may be synthesized in several ways. FIG. 1 depicts an example process for the synthesis of the compound according to Formula I, N-(4-(2-amino-6-oxo-1,6,-dihydro-9H-purin-9-yl)-2-(hydroxymethyl)butyl)-2-(1,4,8,11-tetraazacyclotetradecan-1-yl)acetamide. As shown in FIG. 1, Compound 1 (penciclovir, 50.0 g, 1 Eq, 197 mmol) may be charged in a 1 L flask with a mechanical stirrer, thermocouple, and nitrogen inlet, followed by the addition of DMSO (300 mL, 60093) (dried over 4A MS) and followed by the addition of triethylamine (44.0 g, 60.5 mL, 2.2 Eq, 434 mmol).

The mixture may be stirred for 10 min to give a white suspension. The stirring may then be increased to vigorous (400-500 RPM). MMTrCl (122 g, 2.0 Eq, 395 mmol) may then be added as a solid while maintaining temperature at 20-25° C. over 20 minutes. An ice bath is then used to periodically lower the reaction temperature. Following the addition, the reaction mixture is a thick brown-black solution. After 4 hrs, the reaction mixture is poured into a mixture of 1.5 L DCM and 1 L water. The reaction mixture is then stirred for 5-10 minutes and let settle for 1 hr before separating the layers. The organic layer is diluted with 1 L water, stirred for 5-10 minutes and let settle for 1 hr. After 1 hr, the mixture is filtered and the solids are discarded. The layers are separated and the organic layer is diluted with 1 L water, stirred for 5-10 minutes and let settle for 1 hr. The layers are separated and after 18 hr aging, the organic layer is filtered and the solids discarded. The organic layer is then dried over sodium sulfate (75 g) and filtered and evaporated filtrate on rotavap (50 mBar, 35 C). Dried briefly under direct vacuum to give 150 g crude solids. Purified by flash chromatography on a 1.5 kg Biotage SNAP Ultra (25 uM) cartridge. The resulting compound was analyzed by proton nuclear magnetic resonance ($^1$H NMR), carbon-13 nuclear magnetic resonance ($^{13}$C NMR), and high-resolution mass spectrometry (HRMS) by electrospray ionization (ESI).

Compound 2 (450 mg, 1 Eq, 564 μmol) was dissolved in Pyridine (7.5 mL) in a reaction vial with stir bar, thermocouple. Then p-toluenesulfonyl chloride (613 mg, 5.7 Eq, 3.21 mmol) was added over 10 min (9:40 AM-9:50 AM). Color darkens somewhat, very mild exotherm. Temperature remains between 20-22 C. After 3.5 hrs, diluted reaction mixture with EtOAc (20 mL) and water (10 mL). Wash organic with a further 2×10 mL water. Dried organic layer over Na2SO4 (500 mg-1 g), evaporated to dryness. Azeotroped 2×10 mL toluene. Then azeodry 1×10 mL MeCN to yield a yellow solid. Silica chromatography (14×) using 10 g cartridge, Biotage SNAP ultra. Reaction/column monitoring at 254 nm with lambda all detection. solvent. Dissolve in 1 mL EtOAc, liquid loading. Rinse 2 mL 65% EtOAc/heptane. MPA:hept. MPB:EtOAc. The resulting compound was analyzed by proton nuclear magnetic resonance ($^1$H NMR), carbon-13 nuclear magnetic resonance ($^{13}$C NMR), and high-resolution mass spectrometry (HRMS) by electrospray ionization (ESI).

In a 1 L RBF with stir bar, thermocouple, nitrogen inlet dissolved Compound 3 (53.7 g, 1 Eq) in anhydrous DMF (537 mL, stored over 4A MS) then added sodium azide (5.13 g, 1.4 Eq). Heated to 50 C. After heating for 24 hrs, cooled reaction to room temperature. partitioned mixture between EtOAc (1.5 L) and water (1.5 L). Let settle 1 hr, then split layers. Wash organic 2×1.5 L water further, allowing mixture to settle for 1 hr each time and discarding the rag layer. Dried organic layer over sodium sulfate (57 g). Evaporated on rotavap (35 C, 50 mBar) and dried briefly under direct vacuum to give Compound 4 as a white semisolid, 38.9 g, 75% yield. The resulting compound was analyzed by proton nuclear magnetic resonance ($^1$H NMR), carbon-13 nuclear magnetic resonance ($^{13}$C NMR), and high-resolution mass spectrometry (HRMS) by electrospray ionization (ESI).

In a 50 mL RBF with stir bar, condenser, thermocouple, heating mantle, charge Compound 4 (1.00 g, 1 Eq) then THF (15 mL) and water (1.5 mL). Triphenylphosphine (344 mg, 1.2 Eq) was added, and the mixture was heated to 65 C. After 4 hrs, cool reaction to 25 C, add hydrochloric acid (216 mg, 0.18 mL, 2 Eq). The mixture was heated to 65 C. After 3 hrs, cool to room temperature and filter thru 0.2 uM frit. Separated colorless lower layer, transferred to RBF and evaporated to white residue. Dried in vacuum oven (20 C, −29 inHg) overnight to give Compound 6 as a white solid (351 mg). A qNMR experiment indicates that the material is 62% potent, with the remainder of mass being water (78% adjusted yield). The resulting compound was analyzed by proton nuclear magnetic resonance ($^1$H NMR), carbon-13 nuclear magnetic resonance ($^{13}$C NMR), and high-resolution mass spectrometry (HRMS) by electrospray ionization (ESI).

In a 100 mL RBF, dilute Compound 6 aqueous solution (35.91 g, 29.8 wt %) with 24 g water. Basify to pH 8.1 with 4M NaOH. After 1.5 hrs, add 2 g of celite and filter suspension. Dry solids overnight at ambient temperature (−29 inHg) to give Compound 6 as a white solid. Solids were dissolved in 550 mL 20% DMSO/MeOH and filtered. Filtrate was evaporated on a rotavap (40 C, 50 mBar) and then under direct vacuum to give Compound 6 solution in DMSO (41.61 g, 12.6 wt %). Compound 6 DMSO solution (41.61 g, 12.6 wt %) was further diluted with anhydrous DMSO (73 mL) and then anhydrous DMF (212 mL). Added stir bar, nitrogen inlet, thermocouple. Added TriBocCyclamAA (12.9 g, 1.1 Eq) then DMAP (5.13 g, 2.0 Eq) and stirred until mostly dissolved. Then, added EDC.HCl (8.1 g, 2.0 Eq) in a single portion at 20 C. After 24 hrs, the reaction mixture was diluted with DCM (815 mL), 160 mL water, and 650 mL sat. sodium sulfate. The pH of the aqueous layer was adjusted from 8 to 4 using 6M HCl (~4.5 mL). The biphase was allowed to settle for 1 hr, then the layers were separated. The organic was washed 4× further with 160 mL water, 650 mL sat. sodium sulfate, maintaining the aqueous pH between 4-5 using 6M HCl. The organic layer was dried over sodium sulfate (27 g) and filtered. The sodium sulfate cake was rinsed with 150 mL DCM and the filtrate evaporated on a rotavap (50 mBar, 40 C) then under direct vacuum (−29 inHg) to give 31.34 g pale yellow oil (49.1 wt %, 15.4 g intermediate 6, 92% yield). The resulting compound was analyzed by proton nuclear magnetic resonance ($^1$H NMR), carbon-13 nuclear magnetic resonance ($^{13}$C NMR), and high-resolution mass spectrometry (HRMS) by electrospray ionization (ESI).

As further shown in FIG. 1, Compound 7 is dissolved (13.2 g, 1 Eq) in DCM (190 mL) and MeCN (20 mL) in 1 L flask with stir bar. Add triethylsilane (19.9 mL, 7.5 Eq) then cool to 0C. Add trifluoroacetic acid (51.3 mL, 40 Eq) maintaining temperature <10 C. Following addition warm to room temperature. After 23 hr, charge additional trifluoroacetic acid (12.5 mL, 10 Eq). After 24 hrs, dilute mixture with 40 mL water, stir for 1.5 hr, then let settle for 15 min. Collect faint purple, hazy aqueous lower layer into 1 L RBF. Extract organic additional portion 40 mL water, combine colorless upper aqueous layer with previous aqueous extract. Adjust pH to 8.4 with 4M NaOH, maintaining temperature <35 C. Strip on rotavap (40 C, 50 mBar) then freeze dry overnight to give 180 g crude as an aqueous solution. The resulting compound was analyzed by proton nuclear magnetic resonance ($^1$H NMR), carbon-13 nuclear magnetic resonance ($^{13}$C NMR), and high-resolution mass spectrometry (HRMS) by electrospray ionization (ESI).

Example 2—Synthesis of the Compound According to Formula II, N-(9-(4-amino-3-(hydroxymethyl)butyl)-6-oxo-6,9-dihydro-1H-purin-2-yl)-2-(1,4,8,11-tetraazacyclotetradecan-1-yl)acetamide Synthesis affords the constitutional isomer nucleoside analog compound according to Formula II,

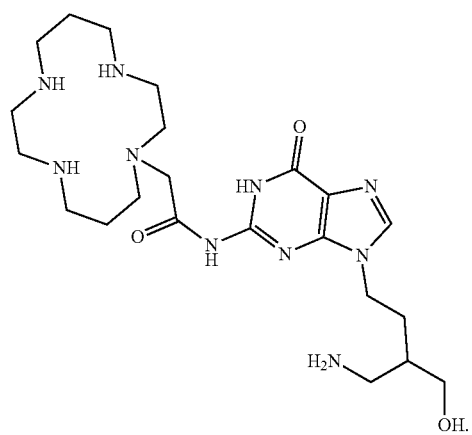

Formula II

Example 3—Synthesis of the Compound According to Formula III, N-(9-(4-(2-(1,4,8,11-tetraazacyclotetradecan-1-yl)acetamido-3-(hydroxymethyl)butyl)-6-oxo-6,9-dihydro-1H-purin-2-yl)-2-(1,4,8,11-tetraazacyclotetradecan-1-yl)acetamide Synthesis affords the dicyclam product nucleoside analog compound according to Formula III,

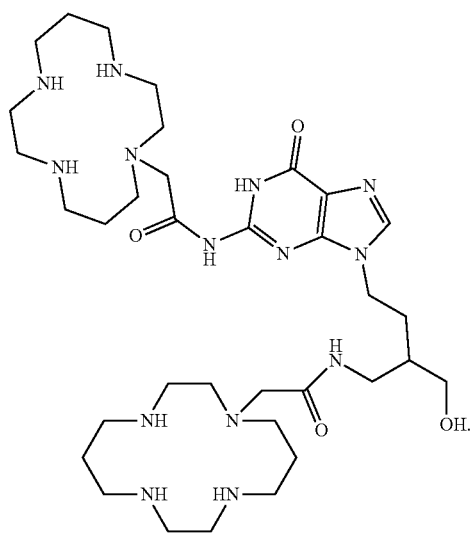

Formula III

Example 4—Synthesis of the Compound According to Formula IV, 1,4,8,11-tetraazacyclotetradecane-1'-acetyl-[N-(piperidin-1-yl)-5-(4-chlorophenyl)-1-(2,4-dichlorophenyl)-4-methyl-1H-pyrazole-3-carboxamide]

The nucleoside analog compound according to Formula IV,

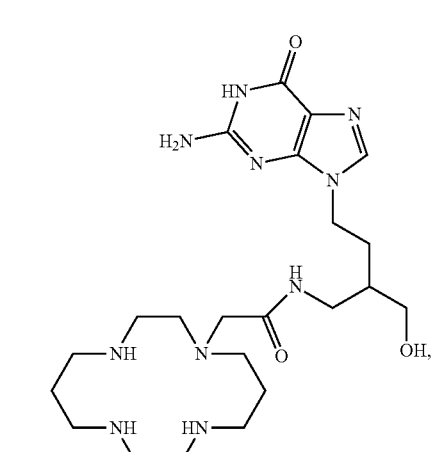

Figure 2:
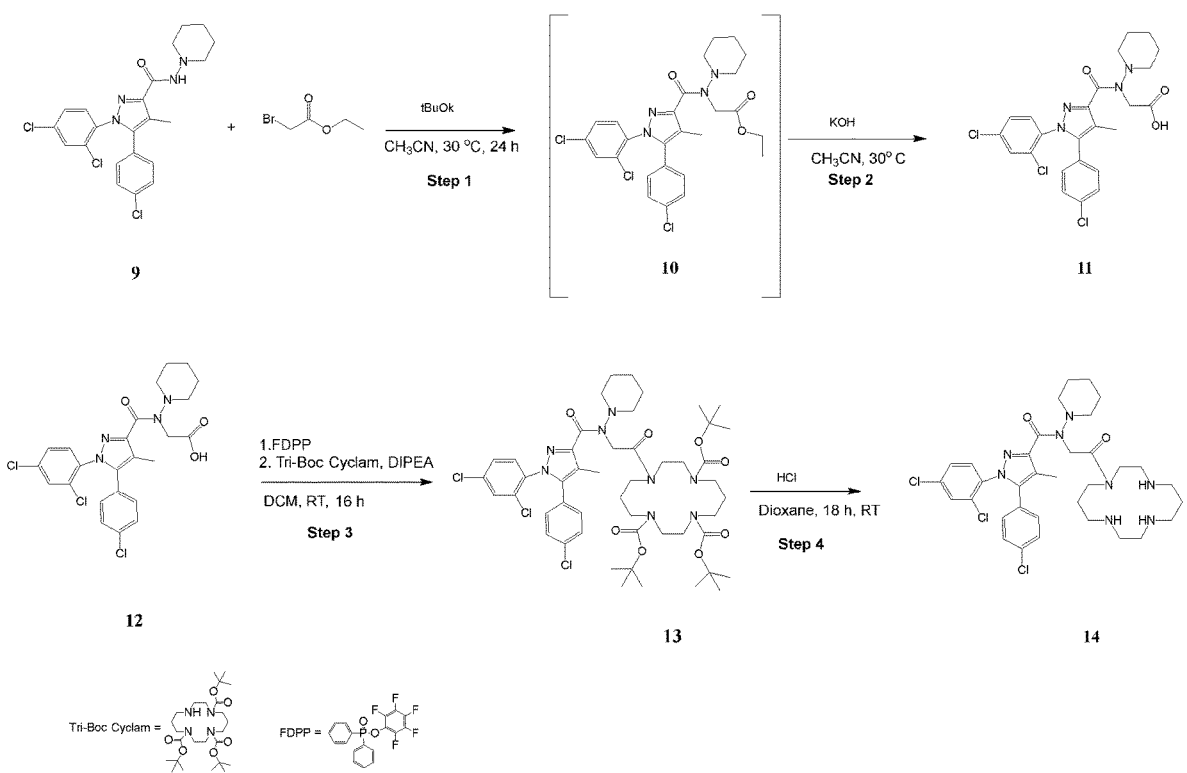
FIG. 2 is an exemplary process for the synthesis of the compound according to structural formula IV, 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carboxamide], according to an exemplary embodiment of the present disclosure.

Formula IV may be synthesized in several ways. FIG. 2 depicts an example process for the synthesis of the compound according to Formula IV, 1,4,8,11-tetraazacyclotetradecane-1'-acetyl[N-(Piperidin-1-yl)-5-(4-chlorophenyl)-1-(2,4-dichlorophenyl)-4-methyl-1H-pyrazole-3-carboxamide].

Statements of the Disclosure Include:

Statement 1: A combination therapy composition comprising: one or more synthetic cannabinoid compounds; and at least one active pharmaceutical ingredient.

Statement 2: The combination therapy composition according to Statement 1, wherein the one or more synthetic cannabinoid compounds comprises a cannabinoid receptor agonist or a cannabinoid receptor antagonist.

Statement 3: The combination therapy composition according to Statement 1, wherein the one or more synthetic cannabinoid compounds comprises an agonist or an antagonist for a cannabinoid receptor.

Statement 4: The combination therapy composition according to Statement 2 or Statement 3, wherein the cannabinoid receptor is an animal cannabinoid receptor.

Statement 5: The combination therapy composition according to Statement 2 or Statement 3, wherein the cannabinoid receptor is a mammalian cannabinoid receptor.

Statement 6: The combination therapy composition according to Statement 2 or Statement 3, wherein the cannabinoid receptor is a human cannabinoid receptor.

Statement 7: The combination therapy composition according to any one of Statements 2-6, wherein the cannabinoid receptor is cannabinoid receptor subtype $CB_1$.

Statement 8: The combination therapy composition according to any one of Statements 2-6, wherein the cannabinoid receptor is cannabinoid receptor subtype $CB_2$.

Statement 9: The combination therapy composition according to any one of Statements 2-6, wherein the cannabinoid receptor is a non-$CB_1$ and a non-$CB_2$ receptor.

Statement 10: The combination therapy composition according to Statement 1, wherein the one or more synthetic cannabinoid compounds comprises a synthetic agonist for cannabinoid receptor subtype $CB_1$.

Statement 11: The combination therapy composition according to Statement 1, wherein the one or more synthetic cannabinoid compounds comprises a synthetic agonist for cannabinoid receptor subtype $CB_2$.

Statement 12: The combination therapy composition according to Statement 1, wherein the one or more synthetic cannabinoid compounds comprises a synthetic antagonist for cannabinoid receptor subtype $CB_1$.

Statement 13: The combination therapy composition according to Statement 1, wherein the one or more synthetic cannabinoid compounds comprises a synthetic antagonist for cannabinoid receptor subtype $CB_2$.

Statement 14: The combination therapy composition according to Statement 1, wherein the one or more synthetic cannabinoid compounds comprises a synthetic agonist for cannabinoid receptor subtype $CB_1$ and a synthetic agonist for cannabinoid receptor subtype $CB_2$.

Statement 15: The combination therapy composition according to Statement 1, wherein the one or more synthetic cannabinoid compounds comprises a synthetic antagonist for cannabinoid receptor subtype $CB_1$ and a synthetic antagonist for cannabinoid receptor subtype $CB_2$.

Statement 16: The combination therapy composition according to Statement 1, wherein the one or more synthetic cannabinoid compounds comprises a synthetic selective $CB_2$ agonist.

Statement 17: The combination therapy composition according to Statement 12, wherein the synthetic antagonist for cannabinoid receptor subtype $CB_1$ comprises a diarylopyrazole compound.

Statement 18: The combination therapy composition according to Statement 12, wherein the synthetic antagonist for cannabinoid receptor subtype $CB_1$ comprises a compound selected from the group consisting of N-(piperidin-1-yl)-5-(4-chlorophenyl)-1-(2,4-dichlorophenyl)-4-methyl-1H-pyrazole-3-carboxamidehydrochloride (SR141716A or Rimonabant), N-(piperdin-1-yl)-5-(4-iodophenyl)-1-(2,4-dichlorophenyl)-4-methyl-1H-pyrazole-3-carboxyamide (AM251), N-(morpholin-4-yl)-1-(2,4-dichlorophenyl)-5-(4-iodophenyl)-4-methyl-1H-pyrazole-3carboxamide (AM281), 4-[6-Methoxy-2-(4-methoxyphenyl)benzofuran-3-carbonyl]benzonitrile (LY320135), and any combination thereof.

Statement 19: The combination therapy composition according to Statement 1 or Statement 14, wherein the one or more synthetic cannabinoid compounds comprises 5-(1,1-Dimethylheptyl)-2-[5-hydroxy-2-(3-hydroxypropyl)cyclohexyl]phenol (CP-55940).

Statement 20: The combination therapy composition according to Statement 1 or Statement 14, wherein the one or more synthetic cannabinoid compounds comprises (6aR,10aR)-6,6,9-trimethyl-3-pentyl-6a,7,8,10a-tetrahydrobenzo[c]chromen-1-ol (Dronabinol or Marinol).

Statement 21: The combination therapy composition according to Statement 1 or Statement 14, wherein the one or more synthetic cannabinoid compounds comprises (6aR,10aR)-1-hydroxy-6,6-dimethyl-3-(2-methyloctan-2-yl)-7,8,10,10a-tetrahydro-6aH-benzo[c]chromen-9-one (Nabilone).

Statement 22: The combination therapy composition according to Statement 1 or Statement 11, wherein the one or more synthetic cannabinoid compounds comprises an aminoalkylindole compound.

Statement 23: The combination therapy composition according to Statement 1 or Statement 11, wherein the one or more synthetic cannabinoid compounds comprises (2-iodo-5-nitrophenyl)-(1-(1-methylpiperidin-2-ylmethyl)-1H-indol-3-yl)methanone (AM1241).

Statement 24: The combination therapy composition according to Statement 1 or Statement 11, wherein the one or more synthetic cannabinoid compounds comprises 4-[4-(1,1-dimethylheptyl)-2,6-dimethoxyphenyl]-6,6-dimethyl-bicyclo[3.1.1]hept-2-ene-2-methanol (HU-308).

Statement 25: The combination therapy composition according to Statement 1, wherein the one or more synthetic cannabinoid compounds comprises (6aR,10aR)-9-(hydroxymethyl)-6,6-dimethyl-3-(2-methyloctan-2-yl)-6a,7,10,10a-tetrahydrobenzo[c]chromen-1-ol (HU-210).

Statement 26: The combination therapy composition according to Statement 1, wherein the one or more synthetic cannabinoid compounds is selected from the group consisting of a diarylopyrazole, N-(piperidin-1-yl)-5-(4-chlorophenyl)-1-(2,4-dichlorophenyl)-4-methyl-1H-pyrazole-3-carboxamidehydrochloride (SR141716A or Rimonabant), N-(piperdin-1-yl)-5-(4-iodophenyl)-1-(2,4-dichlorophenyl)-4-methyl-1H-pyrazole-3-carboxyamide (AM251), N-(morpholin-4-yl)-1-(2,4-dichlorophenyl)-5-(4-iodophenyl)-4-methyl-1H-pyrazole-3carboxamide (AM281), 4-[6-Methoxy-2-(4-methoxyphenyl)benzofuran-3-carbonyl] benzonitrile (LY320135), 5-(1,1-Dimethylheptyl)-2-[5-hydroxy-2-(3-hydroxypropyl)cyclohexyl]phenol (CP-55940), (6aR,10aR)-6,6,9-trimethyl-3-pentyl-6a,7,8,10a-tetrahydrobenzo[c]chromen-1-ol (Dronabinol or Marinol), (6aR,10aR)-1-hydroxy-6,6-dimethyl-3-(2-methyloctan-2-yl)-7,8,10,10a-tetrahydro-6aH-benzo[c]chromen-9-one (Nabilone), an aminoalkylindole, (2-iodo-5-nitrophenyl)-(1-(1-methylpiperidin-2-ylmethyl)-1H-indol-3-yl)methanone (AM1241), 4-[4-(1,1-dimethylheptyl)-2,6-dimethoxyphenyl]-6,6-dimethyl-bicyclo[3.1.1]hept-2-ene-2-methanol (HU-308), (6aR,10aR)-9-(hydroxymethyl)-6,6-dimethyl-3-(2-methyloctan-2-yl)-6a,7,10,10a-tetrahydrobenzo[c]chromen-1-ol (HU-210), (2R,4R,4aR,6 S, 8aS)-6-(Hydroxymethyl)-5-[2-hydroxy-4-(2-methyl-2-octanyl)phenyl]decahydro-2-naphthalenol (CP55244), 2-[(1S,3R)-3-hydroxycyclohexyl]-5-(2-methyloctan-2-yl)phenol (CP47497), (11R)-2-Methyl-11-[(morpholin-4-yl)methyl]-3-(naphthalene-1-carbonyl)-9-oxa-1-azatricyclo[6.3.1.0]dodeca-2,4(12),5,7-tetraene (R—H-WIN55212), (2-Methyl-1-propyl-1H-indol-3-yl)-1-naphthalenylmethanone (JAVH-015), 142,3-Dichlorobenzoyl)-5-methoxy-2-methyl-3-[2-(4-morpholinyl)ethyl]-1H-indole (L-768242), and any combination thereof.

Statement 27: The combination therapy composition according to Statement 1, wherein the one or more synthetic cannabinoid compounds is a synthetic eicosanoid.

Statement 28: The combination therapy composition according to Statement 1 or Statement 27, wherein the one or more synthetic cannabinoid compounds is a synthetic eicosanoid selected from the group consisting of methanandamide (R and S isomers), arachidonyl-2-chloroethylamide (ACEA), arachidonylcyclopropylamide (ACPA), and any combination thereof.

Statement 29: The combination therapy composition according to Statement 1, wherein the one or more synthetic cannabinoid compounds is desacetyl-L-nantradol.

Statement 30: The combination therapy composition according to Statement 1, wherein the one or more synthetic cannabinoid compounds comprises 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carboxamide](VYR206).

Statement 31: The combination therapy composition according to Statement 1, wherein the one or more synthetic cannabinoid compounds comprises a compound having a structure according to Formula IV:

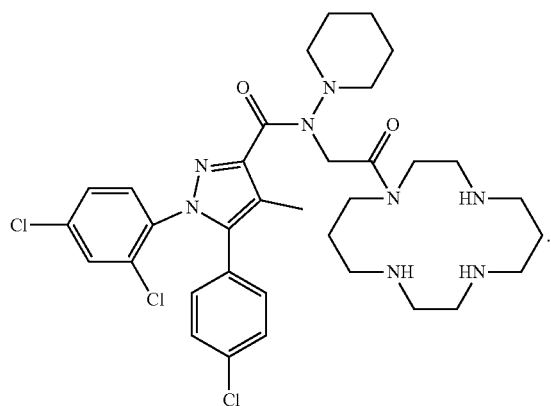

Formula IV

Statement 32: The combination therapy composition according to Statement 16, wherein the synthetic selective $CB_2$ agonist is selected from the group consisting of 4-[4-(1,1-dimethylheptyl)-2,6-dimethoxyphenyl]-6,6-dimethyl-bicyclo[3.1.1]hept-2-ene-2-methanol (HU-308), 3-(1,1-Dimethylbutyl)-1-deoxy-$\Delta^8$-tetrahydrocannabinol (JWH-133), JWH-139, 3-(1,1-dimethylheptyl)-6aR,7,10,10aR-tetrahydro-1-methoxy-6,6,9-trimethyl-6H-dibenzo[b,d]pyran (L-759633), (6aR,10aR)-3-(1,1-Dimethylheptyl)-6a,7,8,9,10,10a-hexahydro-1-methoxy-6,6-dimethyl-9-methyl ene-6H-dibenzo[b,d]pyran (L-759656).

Statement 33. The combination therapy composition according to any one of Statements 1-32, wherein at least one of the one or more synthetic cannabinoid compounds is conjugated to a chelator and a label to form a synthetic cannabinoid-chelator-label conjugate.

Statement 34: The combination therapy composition according to any one of Statements 1-32, wherein at least one of the one or more synthetic cannabinoid compounds is conjugated to a chelator, a label, and a nucleoside analog to form a synthetic cannabinoid-chelator-label-nucleoside analog conjugate.

Statement 35: The combination therapy composition according to Statement 34 wherein the nucleoside analog is a guanine analog.

Statement 36: The combination therapy composition according to Statement 34, wherein the nucleoside analog is a cell replication check point ligand.

Statement 37: The combination therapy composition according to Statement 34, wherein the nucleoside analog is a synthetic analog.

Statement 38: The combination therapy composition according to Statement 34, wherein the nucleoside analog is a natural analog.

Statement 39: The combination therapy composition according to Statement 34, wherein the nucleoside analog is guanine.

Statement 40: The combination therapy composition according to Statement 34, wherein the nucleoside analog is selected from the group consisting of adenine, adenosine, deoxyadenosine, guanine, guanosine, dexoyguanosine, thymine, 5-methyluridine, thymidine, uracile, uridine, deoxyuridine, cytosine, cytidine, deoxycytidine, and any combination thereof.

Statement 41: The combination therapy composition according to Statement 34, wherein the nucleoside analog is arabinosyl nucleoside.

Statement 42: The combination therapy composition according to Statement 34, wherein the conjugate comprises N4-guanine (N4amG).

Statement 43: The combination therapy composition according to Statement 34, wherein the conjugate comprises cyclam-am-guanine.

Statement 44: The combination therapy composition according to Statement 34, wherein the conjugate comprises N-(4-(2-amino-6-oxo-1,6,-dihydro-9H-purin-9-yl)-2-(hydroxymethyl)butyl)-2-(1,4,8,11-tetraazacyclotetradecan-1-yl) acetamide.

Statement 45: The combination therapy composition according to Statement 34, wherein the conjugate comprises a conjugate compound having a structure according to Formula I:

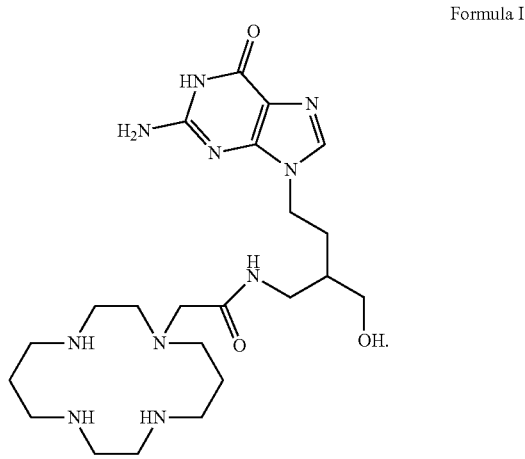 [SMILES: Nc1nc2c(ncn2CCC(CO)CNC(=O)CN2CCCNCCNCCCNCC2)c(=O)[nH]1]

Formula I

Statement 46: The combination therapy composition according to Statement 34, wherein the conjugate comprises N-(9-(4-amino-3-(hydroxymethyl)butyl)-6-oxo-6,9-dihydro-1H-purin-2-yl)-2-(1,4,8,11-tetraazacyclotetradecan-1-yl) acetamide.

Statement 47: The combination therapy composition according to Statement 34, wherein the conjugate comprises a conjugate compound having a structure according to Formula II:

Formula II

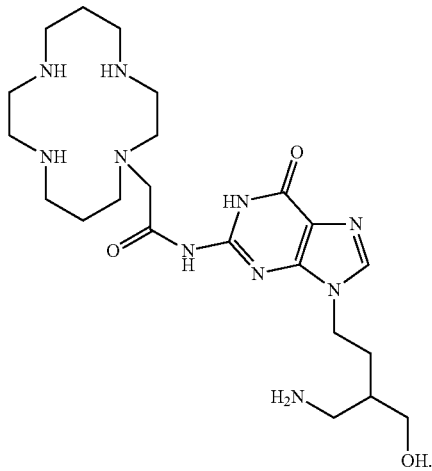

Statement 48: The combination therapy composition according to Statement 34, wherein the conjugate comprises N-(9-(4-(2-(1,4,8,11-tetraazacyclotetradecan-1-yl)acetamido-3-(hydroxymethyl)butyl)-6-oxo-6,9-dihydro-1H-purin-2-yl)-2-(1,4,8,11-tetraazacyclotetradecan-1-yl)acetamide.

Statement 49: The combination therapy composition according to Statement 34, wherein the conjugate comprises a conjugate compound having a structure according to Formula III:

Formula III

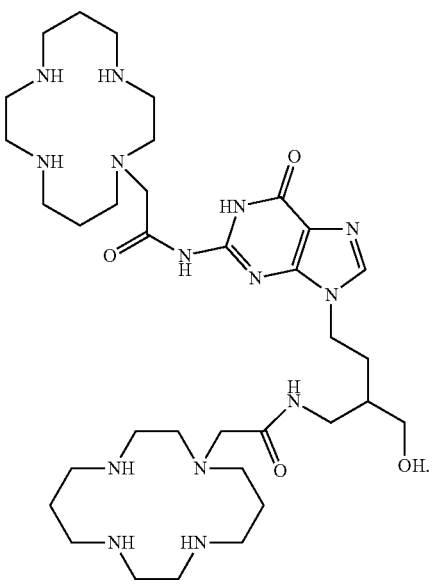

Statement 50: The combination therapy composition according to Statement 34, wherein the conjugate comprises 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carboxamide].

Statement 51: The combination therapy composition according to Statement 34, wherein the conjugate comprises a conjugate compound having a structure according to Formula IV:

Formula IV

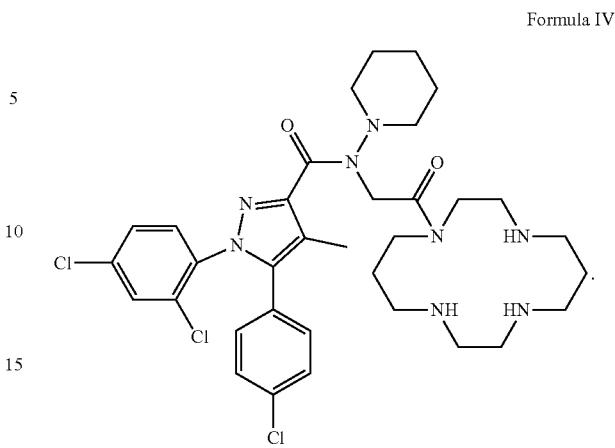

Statement 52: The combination therapy composition according to any one of Statements 33-51, wherein the chelator is an aminated chelator.

Statement 53: The combination therapy composition according to any one of Statements 33-51, wherein the chelator is an acid chelator.

Statement 54: The combination therapy composition according to any one of Statements 33-51, wherein the chelator is cyclam.

Statement 55: The combination therapy composition according to any one of Statements 33-51, wherein the chelator is a N4 chelator or ligand.

Statement 56: The combination therapy composition according to any one of Statements 33-51, wherein the chelator is 6-carboxy-1,4,8,11-tetraazaundecane.

Statement 57: The combination therapy composition according to any one of Statements 33-51, wherein the chelator is 1,4,8,11-tetraazabicyclohexadecane.

Statement 58. The combination therapy composition according to any one of Statements 33-57, wherein the label is a radiotracer label.

Statement 59: The combination therapy composition according to any one of Statements 33-57, wherein the label is a radionuclide.

Statement 60: The combination therapy composition according to any one of Statements 33-57, wherein the label is a non-radioactive metal or a metal selected from the group consisting of rhenium, platinum, copper, iron, arsenic, lead, tantalum, and any combination thereof.

Statement 61: The combination therapy composition according to any one of Statements 33-57, wherein the label is selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof.

Statement 62: The combination therapy composition according to any one of Statements 33-61, wherein the label is configured to facilitate contrast-enhanced imaging when administered to a mammalian subject in conjunction with diagnostic imaging.

Statement 63: The combination therapy composition according to any one of Statements 1-62, further comprising one or more natural cannabinoid compounds.

Statement 64: The combination therapy composition according to Statement 62, wherein the one or more natural cannabinoid compounds is selected from endocannabinoids and phytogenic cannabinoids.

Statement 65: The combination therapy composition according to Statement 63 or Statement 64, wherein the one or more natural cannabinoid compounds is selected from the group of compounds obtained from *Cannabis sativa* or *Cannabis indica* medical marijuana strains.

Statement 66: The combination therapy composition according to Statement 63 or Statement 64, wherein the one or more natural cannabinoid compounds comprises a flavonoid.

Statement 67: The combination therapy composition according to Statement 63 or Statement 64, wherein the one or more natural cannabinoid compounds comprises a terpenoid.

Statement 68: The combination therapy composition according to Statement 64, wherein the one or more natural cannabinoid compounds comprises a phytogenic cannabinoid selected from the group consisting of flavonoids, terpenoids, Nabiximols, Cannador, cannabidiol (CBD), cannabinol (CBN), cannabigerol, tetrahydrocannabivarin, cannabichromene, $\Delta^8$-THC, $\Delta^9$-tetrahydrocannabinol ($\Delta^9$-THC), and any combination thereof.

Statement 69: The combination therapy composition according to Statement 63 or Statement 64, wherein the one or more natural cannabinoid compounds comprises a compound selected from the group consisting of Nabiximols, Cannador, cannabidiol (CBD), cannabinol (CBN), cannabigerol, tetrahydrocannabivarin, cannabichromene, $\Delta^8$-THC, $\Delta^9$-tetrahydrocannabinol ($\Delta^9$-THC), and any combination thereof.

Statement 70: The combination therapy composition according to any one of Statements 63-69, wherein the one or more natural cannabinoid compounds comprises an endocannabinoid compound selected from the group consisting of N-arachidonoylethanolamine, (AEA) or anandamide, 2-arachidonoylglycerol (2-AG), noladin ether, virodhamine, N-arachidonylodopamine (NADA), and any combination thereof.

Statement 71: The combination therapy composition according to any one of Statements 1-70, wherein the at least one active pharmaceutical ingredient is an analgesic.

Statement 72: The combination therapy composition according to Statement 71, wherein the analgesic is selected from the group consisting of nonsteroidal anti-inflammatory drugs (NSAIDs), aspirin, ibuprofen, acetaminophen, naproxen, codeine, salicylates, narcotic analgesics, cyclooxygenase-2 (cox-2) inhibitors, calcitonin gene-related peptide (CGRP) inhibitors, opioids, ziconotide, hydrocodone, oxycodone, fentanyl, morphine, oxymorphone, buprenorphine, levorphanol, tramadol, hydromorphone, methadone, meperidine, propoxyphene, nalbuphine, and any combination thereof.

Statement 73: The combination therapy composition according to any one of Statements 1-70, wherein the at least one active pharmaceutical ingredient is an anti-inflammatory.

Statement 74: The combination therapy composition according to Statement 73, wherein the anti-inflammatory is selected from the group consisting of nonsteroidal anti-inflammatory drugs (NSAIDs), aspirin, ibuprofen, naproxen, corticosteroids, cyclooxygenase-2 (cox-2) inhibitors, salicylates, diclofenac, diflunisal, etodolac, celecoxib, etoricoxib, famotidine, flurbiprofen, indomethacin, ketoprofen, mefenamic acid, meloxicam, nabumetone, oxaprozin, piroxicam, sulindac, glucocorticoids, prednisone, cortisone, hydrocortisone, bethamethasone, prednisolone, triamcinolone, methylprednisolone, dexamethasone, ethamethasoneb, and any combination thereof.

Statement 75: The combination therapy composition according to any one of Statements 1-70, wherein the at least one active pharmaceutical ingredient is an antiviral.

Statement 76: The combination therapy composition according to Statement 75, wherein the antiviral is selected from the group consisting of remdesivir, oseltamivir phosphate, zanamivir, peramivir, baloxavir marboxil, darunavir, atazanavir, ritonavir, acyclovir, valacyclovir, valganciclovir, tenofovir, raltegravir, viral attachment inhibitors, viral entry inhibitors, uncoating inhibitors, protease inhibitors, polymerase inhibitors, nucleoside and nucleotide reverse transcriptase inhibitors, nonnucleoside reverse-transcriptase inhibitors, integrase inhibitors, and any combination thereof.

Statement 77: The combination therapy composition according to any one of Statements 1-76, wherein the combination therapy composition produces at least one synergistic therapeutic effect when administered to a subject.

Statement 78: The combination therapy composition according to Statement 77, wherein the at least one synergistic therapeutic effect is selected from the group consisting of reduced observed toxicity of the at least one active pharmaceutical ingredient, reduction in the administration dosage or amount of active pharmaceutical ingredient required to obtain an advantageous clinical outcome, improved clinical outcomes of the combination therapy as compared to the separate administration of the one or more synthetic cannabinoid compounds or the at least one active pharmaceutical ingredient, and any combination thereof.

Statement 79: A method of treating or alleviating pain in a subject in need thereof, the method comprising: administering to the subject a pharmaceutically effective amount of the combination therapy composition according to any one of Statements 1-72 and 77-78.

Statement 80: A method of treating inflammation in a subject in need thereof, the method comprising: administering to the subject a pharmaceutically effective amount of the combination therapy composition according to any one of Statements 1-70, 73-74, and 77-78.

Statement 81: A method of treating an infectious disease in a subject in need thereof, the method comprising: administering to the subject a pharmaceutically effective amount of the combination therapy composition according to any one of Statements 1-70 and 75-78.

Statement 82: The method according to Statement 81, wherein the infectious disease is a viral infection.

Statement 83: The method according to Statement 81, wherein the infectious disease is a respiratory viral infection selected from the group consisting of human influenza, the common cold, Middle East respiratory syndrome (MERS), severe acute respiratory syndrome coronavirus (SARS), and COVID-19.

Statement 84: The method according to Statement 81, wherein the infectious disease is caused by infection by a virus selected from the group consisting of severe acute respiratory syndrome coronavirus (SARS-CoV), severe acute respiratory syndrome coronavirus 2 (SARS-CoV-2), Middle East respiratory syndrome-related coronavirus (MERS-CoV), human coronavirus NL63 (HCoV NL63), human coronavirus OC43 (HCoV-OC43), human coronavirus HKU1 (HCoV HKU1), and human coronavirus 229E (HCoV-229E).

Statement 85: A method of treating a condition in a subject in need thereof, the method comprising: administering to the subject a pharmaceutically effective amount of the combination therapy composition according to any one of Statements 1-78; wherein the condition is selected from the group consisting of cardiovascular disease, neurological disorders, psychiatric disorders, immunological disorders, endocrine disorders, proliferative and neoplastic disorders, and any combination thereof.

Statement 86: The method according to any one of Statements 79-85, further comprising: performing an imaging technique on the subject or a portion thereof, wherein the imaging technique is capable of detecting one or more signals from the combination therapy composition to generate one or more data images.

Statement 87: The method according to any one of Statement 86, wherein the imaging technique is selected from the group consisting of positron emission tomography (PET), computed tomography (CT), single photon emission computed tomography (SPECT), magnetic resonance imaging (MM), near-infrared (NIR), optical imaging, optoacoustic imaging, ultrasound, and any combination thereof.

Statement 88: The method according to any to Statement 86 or Statement 87, further comprising: making at least one treatment decision based on the one or more data images, wherein the at least one treatment decision is selected from the group consisting of raising or lowering the dose of combination therapy composition administered to the subject, determining the optimal dosage of administration for the particular subject based on the one or more data images, determining whether a dysfunctional pathway or tissue of interest associated with a disease was successfully targeted by the combination therapy composition, determining if an adverse advent was caused by administration of the combination therapy composition, and any combination thereof.

Statement 89: The method according to any to Statement 86 or Statement 87, further comprising: monitoring the uptake of one or more components of the combination therapy composition based on the one or more data images.

Statement 90: The method according to any to Statement 86 or Statement 87, further comprising: wherein the one or more data images provides for visual assessment of uptake at a tissue site of interest of one or more components of the combination therapy composition.

Statement 91: A method of administering a personalized and targeted combination therapy to a subject in need thereof, the method comprising: administering to the subject a pharmaceutically effective amount of a labeled combination therapy composition according to any one of Statements 1-78; performing an imaging technique on the subject or a portion thereof, wherein the imaging technique is capable of detecting one or more signals from the labeled combination therapy composition to generate one or more data images; and making at least one personalized treatment decision based on the one or more data images, wherein the at least one treatment decision is selected from the group consisting of raising or lowering the dose of combination therapy composition administered to the subject, determining the optimal dosage of administration for the particular subject based on the one or more data images, determining whether a dysfunctional pathway or tissue of interest associated with a disease was successfully targeted by the combination therapy composition, determining if an adverse advent was caused by administration of the combination therapy composition, and any combination thereof.

Statement 92: The method according to any one of Statements 79-91, wherein the pharmaceutically effective amount is from about 0.1 to about 1000 mg/kg of body weight per day.

Statement 93: The method according to any one of Statements 79-91, wherein the pharmaceutically effective amount is from about 0.1 to about 750 mg/kg of body weight per day.

Statement 94: The method according to any one of Statements 79-91, wherein the pharmaceutically effective amount is from about 0.1 to about 500 mg/kg of body weight per day.

Statement 95: The method according to any one of Statements 79-91, wherein the pharmaceutically effective amount is from about 0.1 to about 250 mg/kg of body weight per day.

Statement 96: The method according to any one of Statements 79-91, wherein the pharmaceutically effective amount is from about 0.1 to about 100 mg/kg of body weight per day.

Statement 97: The method according to any one of Statements 79-91, wherein the pharmaceutically effective amount is from about 0.1 to about 75 mg/kg of body weight per day.

Statement 98: The method according to any one of Statements 79-91, wherein the pharmaceutically effective amount is from about 0.1 to about 50 mg/kg of body weight per day.

Statement 99: The method according to any one of Statements 79-91, wherein the pharmaceutically effective amount is from about 0.1 to about 30 mg/kg of body weight per day.

Statement 100: The method according to any one of Statements 79-91, wherein the pharmaceutically effective amount is from about 0.1 to about 10 mg/kg of body weight per day.

Statement 101: The method according to any one of Statements 79-91, wherein the pharmaceutically effective amount is from about 0.1 to about 5 mg/kg of body weight per day.

Statement 102: The method according to any one of Statements 79-91, wherein the pharmaceutically effective amount is from about 25 to about 100 mg/kg of body weight per day.

Statement 103: The method according to any one of Statements 79-91, wherein the pharmaceutically effective amount is from about 50 to about 100 mg/kg of body weight per day.

Statement 104: The method according to any one of Statements 79-91, wherein the pharmaceutically effective amount is from about 100 to about 500 mg/kg of body weight per day.

Statement 105: The method according to any one of Statements 79-91, wherein the pharmaceutically effective amount is from about 25 to about 150 mg/kg of body weight per day.

Statement 106: The method according to any one of Statements 79-91, wherein the pharmaceutically effective amount is from about 50 to about 200 mg/kg of body weight per day.

Statement 107: The method according to any one of Statements 79-106, wherein the pharmaceutically effective amount is administered once daily.

Statement 108: The method according to any one of Statements 79-106, wherein the pharmaceutically effective amount is administered twice daily or b.i.d.

Statement 109: The method according to any one of Statements 79-106, wherein the pharmaceutically effective amount is administered three times daily or t.i.d.

Statement 110: The method according to any one of Statements 79-106, wherein the pharmaceutically effective amount is administered four times daily or q.i.d.

Statement 111: The method according to any one of Statements 79-110, wherein the combination therapy composition is administered by an administration route selected from the group consisting of oral, intravenous, sublingual, buccal, rectal, intranasal, parenteral, enteral, transdermal, intramuscular, and any combination thereof.

Statement 112: A labeled synthetic cannabinoid therapeutic composition comprising: a conjugate of a synthetic cannabinoid compound, a chelator, and a label.

Statement 113: The labeled synthetic cannabinoid therapeutic composition according to Statement 112, wherein the synthetic cannabinoid compound comprises a cannabinoid receptor agonist or a cannabinoid receptor antagonist.

Statement 114: The labeled synthetic cannabinoid therapeutic composition according to Statement 112, wherein synthetic cannabinoid compound comprises an agonist or an antagonist for a cannabinoid receptor.

Statement 115: The labeled synthetic cannabinoid therapeutic composition according to Statement 113 or claim 114, wherein the cannabinoid receptor is an animal cannabinoid receptor.

Statement 116: The labeled synthetic cannabinoid therapeutic composition according to Statement 113 or claim 114, wherein the cannabinoid receptor is a mammalian cannabinoid receptor.

Statement 117: The labeled synthetic cannabinoid therapeutic composition according to Statement 113 or claim 114, wherein the cannabinoid receptor is a human cannabinoid receptor.

Statement 118: The labeled synthetic cannabinoid therapeutic composition according to any one of Statements 112-117, wherein the cannabinoid receptor is cannabinoid receptor subtype $CB_1$.

Statement 119: The labeled synthetic cannabinoid therapeutic composition according to any one of Statements 112-117, wherein the cannabinoid receptor is cannabinoid receptor subtype $CB_2$.

Statement 120: The labeled synthetic cannabinoid therapeutic composition according to any one of Statements 112-117, wherein the cannabinoid receptor is a non-$CB_1$ and a non-$CB_2$ receptor.

Statement 121: The labeled synthetic cannabinoid therapeutic composition according to Statement 112, wherein the synthetic cannabinoid compound comprises a synthetic agonist for cannabinoid receptor subtype $CB_1$.

Statement 122: The labeled synthetic cannabinoid therapeutic composition according to Statement 112, wherein the synthetic cannabinoid compound comprises a synthetic agonist for cannabinoid receptor subtype $CB_2$.

Statement 123: The labeled synthetic cannabinoid therapeutic composition according to Statement 112, wherein the synthetic cannabinoid compound comprises a synthetic antagonist for cannabinoid receptor subtype $CB_1$.

Statement 124: The labeled synthetic cannabinoid therapeutic composition according to Statement 112, wherein the synthetic cannabinoid compound comprises a synthetic antagonist for cannabinoid receptor subtype $CB_2$.

Statement 125: The labeled synthetic cannabinoid therapeutic composition according to Statement 112, wherein the synthetic cannabinoid compound comprises a synthetic agonist for cannabinoid receptor subtype $CB_1$ and a synthetic agonist for cannabinoid receptor subtype $CB_2$.

Statement 126: The labeled synthetic cannabinoid therapeutic composition according to Statement 112, wherein the synthetic cannabinoid compound comprises a synthetic antagonist for cannabinoid receptor subtype $CB_1$ and a synthetic antagonist for cannabinoid receptor subtype $CB_2$.

Statement 127: The labeled synthetic cannabinoid therapeutic composition according to Statement 112, wherein the synthetic cannabinoid compound comprises a synthetic selective $CB_2$ agonist.

Statement 128: The labeled synthetic cannabinoid therapeutic composition according to Statement 123, wherein the synthetic antagonist for cannabinoid receptor subtype $CB_1$ comprises a diarylopyrazole compound.

Statement 129: The labeled synthetic cannabinoid therapeutic composition according to Statement 123, wherein the synthetic antagonist for cannabinoid receptor subtype $CB_1$ comprises a compound selected from the group consisting of N-(piperidin-1-yl)-5-(4-chlorophenyl)-1-(2,4-dichlorophenyl)-4-methyl-1H-pyrazole-3-carboxamidehydrochloride (SR141716A or Rimonabant), N-(piperdin-1-yl)-5-(4-iodophenyl)-1-(2,4-dichlorophenyl)-4-methyl-1H-pyrazole-3-carboxyamide (AM251), N-(morpholin-4-yl)-1-(2,4-dichlorophenyl)-5-(4-iodophenyl)-4-methyl-1H-pyrazole-3 carboxamide (AM281), 4-[6-Methoxy-2-(4-methoxyphenyl)benzofuran-3-carbonyl]benzonitrile (LY320135), and any combination thereof.

Statement 130: The labeled synthetic cannabinoid therapeutic composition according to Statement 112 or Statement 125, wherein the synthetic cannabinoid compound comprises 5-(1,1-Dimethylheptyl)-2-[5-hydroxy-2-(3-hydroxypropyl)cyclohexyl]phenol (CP-55940).

Statement 131: The labeled synthetic cannabinoid therapeutic composition according to Statement 112 or Statement 125, wherein the synthetic cannabinoid compound comprises (6aR,10aR)-6,6,9-trimethyl-3-pentyl-6a,7,8,10a-tetrahydrobenzo[c]chromen-1-ol (Dronabinol or Marinol).

Statement 132: The labeled synthetic cannabinoid therapeutic composition according to Statement 112 or Statement 125, wherein the synthetic cannabinoid compound comprises (6aR,10aR)-1-hydroxy-6,6-dimethyl-3-(2-methyloctan-2-yl)-7,8,10,10a-tetrahydro-6aH-benzo[c]chromen-9-one (Nabilone).

Statement 133: The labeled synthetic cannabinoid therapeutic composition according to Statement 112 or Statement 122, wherein the synthetic cannabinoid compound comprises an aminoalkylindole compound.

Statement 134: The labeled synthetic cannabinoid therapeutic composition according to Statement 112 or Statement 122, wherein the synthetic cannabinoid compound comprises (2-iodo-5-nitrophenyl)-(1-(1-methylpiperidin-2-ylmethyl)-1H-indol-3-yl)methanone (AM1241).

Statement 135: The labeled synthetic cannabinoid therapeutic composition according to Statement 112 or Statement 122, wherein the synthetic cannabinoid compound comprises 4-[4-(1,1-dimethylheptyl)-2,6-dimethoxyphenyl]-6,6-dimethyl-bicyclo[3.1.1]hept-2-ene-2-methanol (HU-308).

Statement 136: The labeled synthetic cannabinoid therapeutic composition according to Statement 112, wherein the synthetic cannabinoid compound comprises (6aR,10aR)-9-(hydroxymethyl)-6,6-dimethyl-3-(2-methyloctan-2-yl)-6a,7,10,10a-tetrahydrobenzo[c]chromen-1-ol (HU-210).

Statement 137: The labeled synthetic cannabinoid therapeutic composition according to Statement 112, wherein the synthetic cannabinoid compound is selected from the group consisting of a diarylopyrazole, N-(piperidin-1-yl)-5-(4-chlorophenyl)-1-(2,4-dichlorophenyl)-4-methyl-1H-pyrazole-3-carboxamidehydrochloride (SR141716A or Rimonabant), N-(piperdin-1-yl)-5-(4-iodophenyl)-1-(2,4-dichlorophenyl)-4-methyl-1H-pyrazole-3-carboxyamide (AM251), N-(morpholin-4-yl)-1-(2,4-dichlorophenyl)-5-(4-iodophenyl)-4-methyl-1H-pyrazole-3 carboxamide (AM281), 4-[6-Methoxy-2-(4-methoxyphenyl)benzofuran-3-carbonyl]benzonitrile (LY320135), 5-(1,1-Dimethylheptyl)-2-[5-hydroxy-2-(3-hydroxypropyl)cyclohexyl]phenol (CP-55940), (6aR,10aR)-6,6,9-trimethyl-3-pentyl-6a,7,8,10a-tetrahydrobenzo[c]chromen-1-ol (Dronabinol or Marinol), (6aR,10aR)-1-hydroxy-6,6-dimethyl-3-(2-methyloctan-2-yl)-7,8,10,10a-tetrahydro-6aH-benzo[c]chromen-9-one (Nabilone), an aminoalkylindole, (2-iodo-5-nitrophenyl)-(1-(1-methylpiperidin-2-ylmethyl)-1H-indol-3-yl)methanone (AM1241), 4-[4-(1,1-dimethylheptyl)-2,6-dimethoxyphenyl]-6,6-dimethyl-bicyclo[3.1.1]hept-2-ene-2-methanol (HU-308), (6aR,10aR)-9-(hydroxymethyl)-6,6- dimethyl-3-(2-methyloctan-2-yl)-6a,7,10,10a-tetrahydrobenzo[c]chromen-1-ol (HU-210), (2R,4R,4aR,6S,8aS)-6-(Hydroxymethyl)-4-[2-hydroxy-4-(2-methyl-2-octanyl)phenyl]decahydro-2-naphthalenol (CP55244), 2-[(1S,3R)-3-hydroxycyclohexyl]-5-(2-methyloctan-2-yl)phenol (CP47497), (11R)-2-Methyl-11-[(morpholin-4-yl)methyl]-3-(naphthalene-1-carbonyl)-9-oxa-1-azatricyclo[6.3.1.0]dodeca-2,4(12), 5,7-tetraene (R-(+)-WIN55212), (2-Methyl-1-propyl-1H-indol-3-yl)-1-naphthalenylmethanone (JWH-015), 142,3-Dichlorobenzoyl)-5-methoxy-2-methyl-3-[2-(4-morpholinyl)ethyl]-1H-indole (L-768242), and any combination thereof.

Statement 138: The labeled synthetic cannabinoid therapeutic composition according to Statement 112, wherein the synthetic cannabinoid compound is a synthetic eicosanoid.

Statement 139: The labeled synthetic cannabinoid therapeutic composition according to Statement 112 or Statement 138, wherein synthetic cannabinoid compound is a synthetic eicosanoid selected from the group consisting of methanandamide (R and S isomers), arachidonyl-2-chloroethylamide (ACEA), arachidonylcyclopropylamide (ACPA), and any combination thereof.

Statement 140: The labeled synthetic cannabinoid therapeutic composition according to Statement 112, wherein the synthetic cannabinoid compound is desacetyl-L-nantradol.

Statement 141: The labeled synthetic cannabinoid therapeutic composition according to Statement 112, wherein the synthetic cannabinoid compound comprises 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carb oxamide](VYR206).

Statement 142: The labeled synthetic cannabinoid therapeutic composition according to Statement 112, wherein the synthetic cannabinoid compound comprises a compound having a structure according to Formula IV:

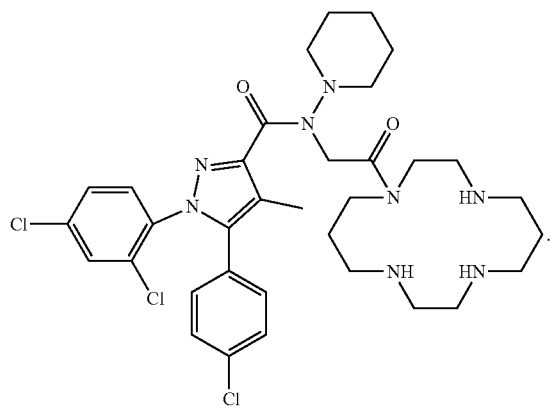

Formula IV

Statement 143: The labeled synthetic cannabinoid therapeutic composition according to Statement 127, wherein the synthetic selective $CB_2$ agonist is selected from the group consisting of 4-[4-(1,1-dimethylheptyl)-2,6-dimethoxyphenyl]-6,6-dimethyl-bicyclo[3.1.1]hept-2-ene-2-methanol (HU-308), 3-(1,1-Dimethylbutyl)-1-deoxy-$\Delta^8$-tetrahydrocannabinol (JWH-133), JWH-139, 3-(1,1-dimethylheptyl)-6aR,7,10,10aR-tetrahydro-1-methoxy-6,6,9-trimethyl-6H-dibenzo[b,d]pyran (L-759633), (6aR,10aR)-3-(1,1-Dimethylheptyl)-6a,7,8,9,10,10a-hexahydro-1-methoxy-6,6-dimethyl-9-methylene-6H-dibenzo[b,d]pyran (L-759656).

Statement 144: The labeled synthetic cannabinoid therapeutic composition according to any one of Statements 112-143, wherein the synthetic cannabinoid compound is further conjugated to a nucleoside analog to form a synthetic cannabinoid-chelator-label-nucleoside analog conjugate.

Statement 145: The labeled synthetic cannabinoid therapeutic composition according to Statement 144, wherein the nucleoside analog is a guanine analog.

Statement 146: The labeled synthetic cannabinoid therapeutic composition according to Statement 144, wherein the nucleoside analog is a cell replication check point ligand.

Statement 147: The labeled synthetic cannabinoid therapeutic composition according to Statement 144, wherein the nucleoside analog is a synthetic analog.

Statement 148: The labeled synthetic cannabinoid therapeutic composition according to Statement 144, wherein the nucleoside analog is a natural analog.

Statement 149: The labeled synthetic cannabinoid therapeutic composition according to Statement 144, wherein the nucleoside analog is guanine.

Statement 150: The labeled synthetic cannabinoid therapeutic composition according to Statement 144, wherein the nucleoside analog is selected from the group consisting of adenine, adenosine, deoxyadenosine, guanine, guanosine, dexoyguanosine, thymine, 5-methyluridine, thymidine, uracile, uridine, deoxyuridine, cytosine, cytidine, deoxycytidine, and any combination thereof.

Statement 151: The labeled synthetic cannabinoid therapeutic composition according to Statement 144, wherein the nucleoside analog is arabinosyl nucleoside.

Statement 152: The labeled synthetic cannabinoid therapeutic composition according to Statement 144, wherein the conjugate comprises N4-guanine (N4amG).

Statement 153: The labeled synthetic cannabinoid therapeutic composition according to Statement 144, wherein the conjugate comprises cyclam-am-guanine.

Statement 154: The labeled synthetic cannabinoid therapeutic composition according to Statement 144, wherein the conjugate comprises N-(4-(2-amino-6-oxo-1,6,-dihydro-9H-purin-9-yl)-2-(hydroxymethyl)butyl)-2-(1,4,8,11-tetraazacyclotetradecan-1-yl)acetamide.

Statement 155: The labeled synthetic cannabinoid therapeutic composition according to Statement 144, wherein the conjugate comprises a conjugate compound having a structure according to Formula I:

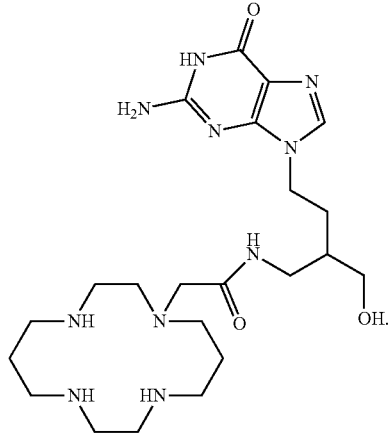

Formula I

Statement 156: The labeled synthetic cannabinoid therapeutic composition according to Statement 144, wherein the conjugate comprises N-(9-(4-amino-3-(hydroxymethyl)

butyl)-6-oxo-6,9-dihydro-1H-purin-2-yl)-2-(1,4,8,11-tet-raazacyclotetradecan-1-yl)acetamide.

Statement 157: The labeled synthetic cannabinoid therapeutic composition according to Statement 144, wherein the conjugate comprises a conjugate compound having a structure according to Formula II:

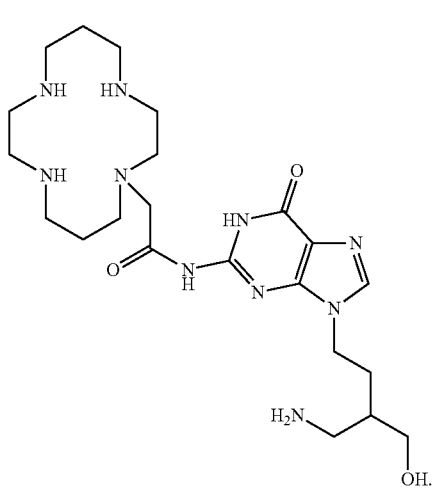

Formula II

Statement 158: The labeled synthetic cannabinoid therapeutic composition according to Statement 144, wherein the conjugate comprises N-(9-(4-(2-(1,4,8,11-tetraazacyclotetradecan-1-yl)acetamido-3-(hydroxy methyl)butyl)-6-oxo-6,9-dihydro-1H-purin-2-yl)-2-(1,4,8,11-tetraazacyclotetradecan-1-yl)acetamide.

Statement 159: The labeled synthetic cannabinoid therapeutic composition according to Statement 144, wherein the conjugate comprises a conjugate compound having a structure according to Formula III:

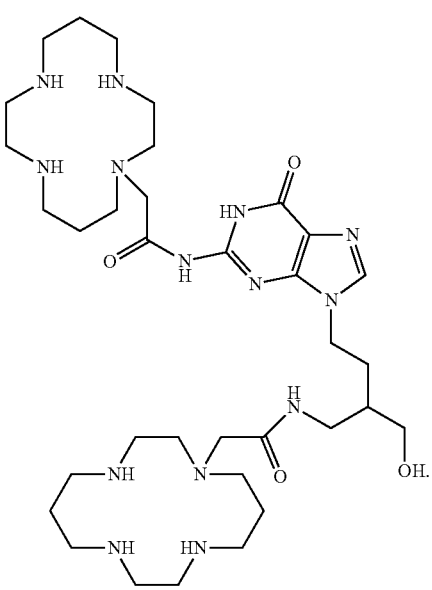

Formula III

Statement 160: The labeled synthetic cannabinoid therapeutic composition according to Statement 144, wherein the conjugate comprises 1,4,8,11-tetraazacyclotetradecane-1'-acetyl-[N-(Piperidin-1-yl)-5-(4-chlorophenyl)-1-(2,4-dichlorophenyl)-4-methyl-1H-pyrazole-3-carboxamide].

Statement 161: The labeled synthetic cannabinoid therapeutic composition according to Statement 144, wherein the conjugate comprises a conjugate compound having a structure according to Formula IV:

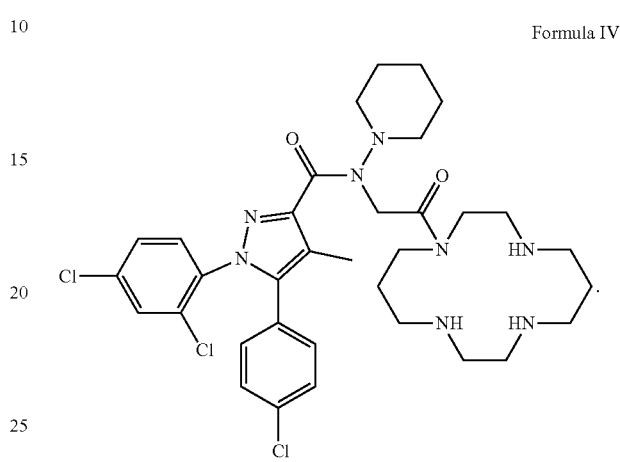

Formula IV

Statement 162: The labeled synthetic cannabinoid therapeutic composition according to any one of Statements 112-161, wherein the chelator is an aminated chelator.

Statement 163: The labeled synthetic cannabinoid therapeutic composition according to any one of Statements 112-161, wherein the chelator is an acid chelator.

Statement 164: The labeled synthetic cannabinoid therapeutic composition according to any one of Statements 112-161, wherein the chelator is cyclam.

Statement 165: The labeled synthetic cannabinoid therapeutic composition according to any one of Statements 112-161, wherein the chelator is a N4 chelator or ligand.

Statement 166: The labeled synthetic cannabinoid therapeutic composition according to any one of Statements 112-161, wherein the chelator is 6-carboxy-1,4,8,11-tetraazaundecane.

Statement 167: The labeled synthetic cannabinoid therapeutic composition according to any one of Statements 112-161, wherein the chelator is 1,4,8,11-tetraazabicyclohexadecane.

Statement 168: The labeled synthetic cannabinoid therapeutic composition according to any one of Statements 112-167, wherein the label is a radiotracer label.

Statement 169: The labeled synthetic cannabinoid therapeutic composition according to any one of Statements 112-167, wherein the label is a radionuclide.

Statement 170: The labeled synthetic cannabinoid therapeutic composition according to any one of Statements 112-167, wherein the label is a non-radioactive metal or a metal selected from the group consisting of rhenium, platinum, copper, iron, arsenic, lead, tantalum, and any combination thereof.

Statement 171: The labeled synthetic cannabinoid therapeutic composition according to any one of Statements 112-167, wherein the label is selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof.

Statement 172: The labeled synthetic cannabinoid therapeutic composition according to any one of Statements 112-167, wherein the label is configured to facilitate contrast-enhanced imaging when administered to a mammalian subject in conjunction with diagnostic imaging.

Statement 173: The labeled synthetic cannabinoid therapeutic composition according to any one of Statements 112-172, further comprising one or more natural cannabinoid compounds.

Statement 174: The labeled synthetic cannabinoid therapeutic composition according to Statement 173, wherein the one or more natural cannabinoid compounds is selected from endocannabinoids and phytogenic cannabinoids.

Statement 175: The labeled synthetic cannabinoid therapeutic composition according to Statement 173 or Statement 174, wherein the one or more natural cannabinoid compounds is selected from the group of compounds obtained from *Cannabis sativa* or *Cannabis indica* medical marijuana strains.

Statement 176: The labeled synthetic cannabinoid therapeutic composition according to Statement 173 or Statement 174, wherein the one or more natural cannabinoid compounds comprises a flavonoid.

Statement 177: The labeled synthetic cannabinoid therapeutic composition according to Statement 173 or Statement 174, wherein the one or more natural cannabinoid compounds comprises a terpenoid.

Statement 178: The labeled synthetic cannabinoid therapeutic composition according to Statement 174, wherein the one or more natural cannabinoid compounds comprises a phytogenic cannabinoid selected from the group consisting of flavonoids, terpenoids, Nabiximols, Cannador, cannabidiol (CBD), cannabinol (CBN), cannabigerol, tetrahydrocannabivarin, cannabichromene, $\Delta^8$-THC, $\Delta^9$-tetrahydrocannabinol ($\Delta^9$-THC), and any combination thereof.

Statement 179: The labeled synthetic cannabinoid therapeutic composition according to Statement 173 or Statement 174, wherein the one or more natural cannabinoid compounds comprises a compound selected from the group consisting of Nabiximols, Cannador, cannabidiol (CBD), cannabinol (CBN), cannabigerol, tetrahydrocannabivarin, cannabichromene, $\Delta^8$-THC, $\Delta^9$-tetrahydrocannabinol ($\Delta^9$-THC), and any combination thereof.

Statement 180: The labeled synthetic cannabinoid therapeutic composition according to any one of Statements 173-179, wherein the one or more natural cannabinoid compounds comprises an endocannabinoid compound selected from the group consisting of N-arachidonoylethanolamine, (AEA) or anandamide, 2-arachidonoylglycerol (2-AG), noladin ether, virodhamine, N-arachidonylodopamine (NADA), and any combination thereof.

Statement 181: The labeled synthetic cannabinoid therapeutic composition according to any one of Statements 112-180, further comprising at least one active pharmaceutical ingredient.

Statement 182: The labeled synthetic cannabinoid therapeutic composition according to Statement 181, wherein the at least one active pharmaceutical ingredient is an analgesic.

Statement 183: The labeled synthetic cannabinoid therapeutic composition according to Statement 182, wherein the analgesic is selected from the group consisting of nonsteroidal anti-inflammatory drugs (NSAIDs), aspirin, ibuprofen, acetaminophen, naproxen, codeine, salicylates, narcotic analgesics, cyclooxygenase-2 (cox-2) inhibitors, calcitonin gene-related peptide (CGRP) inhibitors, opioids, ziconotide, hydrocodone, oxycodone, fentanyl, morphine, oxymorphone, buprenorphine, levorphanol, tramadol, hydromorphone, methadone, meperidine, propoxyphene, nalbuphine, and any combination thereof.

Statement 184: The labeled synthetic cannabinoid therapeutic composition according to Statement 181, wherein the at least one active pharmaceutical ingredient is an anti-inflammatory.

Statement 185: The labeled synthetic cannabinoid therapeutic composition according to Statement 184, wherein the anti-inflammatory is selected from the group consisting of nonsteroidal anti-inflammatory drugs (NSAIDs), aspirin, ibuprofen, naproxen, corticosteroids, cyclooxygenase-2 (cox-2) inhibitors, salicylates, diclofenac, diflunisal, etodolac, celecoxib, etoricoxib, famotidine, flurbiprofen, indomethacin, ketoprofen, mefenamic acid, meloxicam, nabumetone, oxaprozin, piroxicam, sulindac, glucocorticoids, prednisone, cortisone, hydrocortisone, bethamethasone, prednisolone, triamcinolone, methylprednisolone, dexamethasone, ethamethasoneb, and any combination thereof.

Statement 186: The labeled synthetic cannabinoid therapeutic composition according to Statement 181, wherein the at least one active pharmaceutical ingredient is an antiviral.

Statement 187: The labeled synthetic cannabinoid therapeutic composition according to Statement 186, wherein the antiviral is selected from the group consisting of remdesivir, oseltamivir phosphate, zanamivir, peramivir, baloxavir marboxil, darunavir, atazanavir, ritonavir, acyclovir, valacyclovir, valganciclovir, tenofovir, raltegravir, viral attachment inhibitors, viral entry inhibitors, uncoating inhibitors, protease inhibitors, polymerase inhibitors, nucleoside and nucleotide reverse transcriptase inhibitors, nonnucleoside reverse-transcriptase inhibitors, integrase inhibitors, and any combination thereof.

Statement 188: A method of treating or alleviating pain in a subject in need thereof, the method comprising: administering to the subject a pharmaceutically effective amount of the labeled synthetic cannabinoid therapeutic composition according to any one of Statements 112-187.

Statement 189: A method of treating inflammation in a subject in need thereof, the method comprising: administering to the subject a pharmaceutically effective amount of the labeled synthetic cannabinoid therapeutic composition according to any one of Statements 112-187.

Statement 190: A method of treating an infectious disease in a subject in need thereof, the method comprising: administering to the subject a pharmaceutically effective amount of the labeled synthetic cannabinoid therapeutic composition according to any one of Statements 112-187.

Statement 191: The method according to Statement 190, wherein the infectious disease is a viral infection.

Statement 192: The method according to Statement 190, wherein the infectious disease is a respiratory viral infection selected from the group consisting of human influenza, the common cold, Middle East respiratory syndrome (MERS), severe acute respiratory syndrome coronavirus (SARS), and COVID-19.

Statement 193: The method according to Statement 190, wherein the infectious disease is caused by infection by a virus selected from the group consisting of severe acute respiratory syndrome coronavirus (SARS-CoV), severe acute respiratory syndrome coronavirus 2 (SARS-CoV-2), Middle East respiratory syndrome-related coronavirus (MERS-CoV), human coronavirus NL63 (HCoV NL63), human coronavirus OC43 (HCoV-OC43), human coronavirus HKU1 (HCoV HKU1), and human coronavirus 229E (HCoV-229E).

Statement 194: A method of treating a condition in a subject in need thereof, the method comprising: administering to the subject a pharmaceutically effective amount of the labeled synthetic cannabinoid therapeutic composition according to any one of Statements 112-187; wherein the condition is selected from the group consisting of cardiovascular disease, neurological disorders, psychiatric disorders, immunological disorders, endocrine disorders, proliferative and neoplastic disorders, and any combination thereof.

Statement 195: The method according to any one of Statements 188-194, further comprising: performing an imaging technique on the subject or a portion thereof, wherein the imaging technique is capable of detecting one or more signals from the labeled synthetic cannabinoid therapeutic composition to generate one or more data images.

Statement 196: The method according to any one of Statement 195, wherein the imaging technique is selected from the group consisting of positron emission tomography (PET), computed tomography (CT), single photon emission computed tomography (SPECT), magnetic resonance imaging (MM), near-infrared (NIR), optical imaging, optoacoustic imaging, ultrasound, and any combination thereof.

Statement 197: The method according to Statement 195 or Statement 196, further comprising: making at least one treatment decision based on the one or more data images, wherein the at least one treatment decision is selected from the group consisting of raising or lowering the dose of combination therapy composition administered to the subject, determining the optimal dosage of administration for the particular subject based on the one or more data images, determining whether a dysfunctional pathway or tissue of interest associated with a disease was successfully targeted by the combination therapy composition, determining if an adverse advent was caused by administration of the combination therapy composition, and any combination thereof.

Statement 198: The method according to any to Statement 195 or Statement 196, further comprising: monitoring the uptake of one or more components of the labeled synthetic cannabinoid therapeutic composition based on the one or more data images.

Statement 199: The method according to any to Statement 195 or Statement 196, further comprising: wherein the one or more data images provides for visual assessment of uptake at a tissue site of interest of one or more components of the labeled synthetic cannabinoid therapeutic composition.

Statement 200: A method of providing a personalized and targeted therapy to a subject in need thereof, the method comprising: administering to the subject a pharmaceutically effective amount of a labeled synthetic cannabinoid therapeutic composition according to any one of Statements 112-187; performing an imaging technique on the subject or a portion thereof, wherein the imaging technique is capable of detecting one or more signals from the labeled synthetic cannabinoid therapeutic composition to generate one or more data images; and making at least one personalized treatment decision based on the one or more data images, wherein the at least one treatment decision is selected from the group consisting of raising or lowering the dose of combination therapy composition administered to the subject, determining the optimal dosage of administration for the particular subject based on the one or more data images, determining whether a dysfunctional pathway or tissue of interest associated with a disease was successfully targeted by the combination therapy composition, determining if an adverse advent was caused by administration of the combination therapy composition, and any combination thereof.

Statement 201: The method according to any one of Statements 188-200, wherein the pharmaceutically effective amount is from about 0.1 to about 1000 mg/kg of body weight per day.

Statement 202: The method according to any one of Statements 188-200, wherein the pharmaceutically effective amount is from about 0.1 to about 750 mg/kg of body weight per day.

Statement 203: The method according to any one of Statements 188-200, wherein the pharmaceutically effective amount is from about 0.1 to about 500 mg/kg of body weight per day.

Statement 204: The method according to any one of Statements 188-200, wherein the pharmaceutically effective amount is from about 0.1 to about 250 mg/kg of body weight per day.

Statement 205: The method according to any one of Statements 188-200, wherein the pharmaceutically effective amount is from about 0.1 to about 100 mg/kg of body weight per day.

Statement 206: The method according to any one of Statements 188-200, wherein the pharmaceutically effective amount is from about 0.1 to about 75 mg/kg of body weight per day.

Statement 207: The method according to any one of Statements 188-200, wherein the pharmaceutically effective amount is from about 0.1 to about 50 mg/kg of body weight per day.

Statement 208: The method according to any one of Statements 188-200, wherein the pharmaceutically effective amount is from about 0.1 to about 30 mg/kg of body weight per day.

Statement 209: The method according to any one of Statements 188-200, wherein the pharmaceutically effective amount is from about 0.1 to about 10 mg/kg of body weight per day.

Statement 210: The method according to any one of Statements 188-200, wherein the pharmaceutically effective amount is from about 0.1 to about 5 mg/kg of body weight per day.

Statement 211: The method according to any one of Statements 188-200, wherein the pharmaceutically effective amount is from about 25 to about 100 mg/kg of body weight per day.

Statement 212: The method according to any one of Statements 188-200, wherein the pharmaceutically effective amount is from about 50 to about 100 mg/kg of body weight per day.

Statement 213: The method according to any one of Statements 188-200, wherein the pharmaceutically effective amount is from about 100 to about 500 mg/kg of body weight per day.

Statement 214: The method according to any one of Statements 188-200, wherein the pharmaceutically effective amount is from about 25 to about 150 mg/kg of body weight per day.

Statement 215: The method according to any one of Statements 188-200, wherein the pharmaceutically effective amount is from about 50 to about 200 mg/kg of body weight per day.

Statement 216: The method according to any one of Statements 188-215, wherein the pharmaceutically effective amount is administered once daily.

Statement 217: The method according to any one of Statements 188-215, wherein the pharmaceutically effective amount is administered twice daily or b.i.d.

Statement 218: The method according to any one of Statements 188-215, wherein the pharmaceutically effective amount is administered three times daily or t.i.d.

Statement 219: The method according to any one of Statements 188-215, wherein the pharmaceutically effective amount is administered four times daily or q.i.d.

Statement 220: The method according to any one of Statements 188-219, wherein the labeled synthetic cannabinoid therapeutic composition is administered by an administration route selected from the group consisting of oral, intravenous, sublingual, buccal, rectal, intranasal, parenteral, enteral, transdermal, intramuscular, and any combination thereof.

Statement 221: The method according to any one of Statements 188-220, wherein the label is a radiotherapeutic label capable of delivering radiation to a tissue in the subject targeted by the conjugate.

Statement 222: The method according to any one of Statements 188-220, wherein the label is a non-radioactive metal capable of providing an advantageous therapeutic response at a tissue in the subject targeted by the conjugate.

Statement 223: The method according to Statement 222, wherein the advantageous therapeutic response is toxicity-induced cell death or viral particle inactivation, reduced viral replication, and/or reduced viral load in the tissue.

Statement 224: The method according to Statement 222 or Statement 223, wherein the non-radioactive metal is selected from the group consisting of rhenium, platinum, copper, iron, arsenic, lead, tantalum, and any combination thereof.

Statement 225: A method of treating an infectious disease in a subject in need thereof, the method comprising: administering to the subject a pharmaceutically effective amount of the labeled synthetic cannabinoid therapeutic composition according to any one of Statements 112-187; wherein the label provides an advantageous therapeutic effect in treating the infectious disease.

Statement 226: The method according to Statement 225, wherein the label is a radiotherapeutic label capable of delivering radiation to an infected tissue in the subject and the advantageous therapeutic effect is increased viral particle inactivation, reduced viral replication, and/or reduced viral load in the tissue.

Statement 227: The method according to Statement 226, wherein the label is selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof.

Statement 228: The method according to Statement 225, wherein the label is a non-radioactive metal that is toxic to an infectious diseases causing agent and the advantageous therapeutic effect is toxicity-induced cell death or viral particle inactivation, reduced viral replication, and/or reduced viral load in the tissue.

Statement 229: The method according to Statement 228, wherein the non-radioactive metal is selected from the group consisting of rhenium, platinum, copper, iron, arsenic, lead, tantalum, and any combination thereof.

Statement 230: The method according to any one of Statements 225-229, wherein the infectious disease is a viral infection.

Statement 231: The method according to any one of Statements 225-229, wherein the infectious disease is a respiratory viral infection selected from the group consisting of human influenza, the common cold, Middle East respiratory syndrome (MERS), severe acute respiratory syndrome coronavirus (SARS), and COVID-19.

Statement 232: The method according to any one of Statements 225-229, wherein the infectious disease is caused by infection by a virus selected from the group consisting of severe acute respiratory syndrome coronavirus (SARS-CoV), severe acute respiratory syndrome coronavirus 2 (SARS-CoV-2), Middle East respiratory syndrome-related coronavirus (MERS-CoV), human coronavirus NL63 (HCoV NL63), human coronavirus OC43 (HCoV-OC43), human coronavirus HKU1 (HCoV HKU1), and human coronavirus 229E (HCoV-229E).

Statement 233: The method according to any one of Statements 79-110, wherein the label is a radiotherapeutic label that delivers radiation to a tissue in the subject targeted by the conjugate.

Statement 234: The method according to any one of Statements 79-110, wherein the label is a non-radioactive metal capable of providing a therapeutic response at a tissue in the subject targeted by the conjugate.

Statement 235: The method according to Statement 234, wherein the therapeutic response is toxicity-induced cell death or viral particle inactivation, reduced viral replication, and/or reduced viral load in the tissue.

Statement 236: The method according to Statement 234 or Statement 235, wherein the non-radioactive metal is selected from the group consisting of rhenium, platinum, copper, iron, arsenic, lead, tantalum, and any combination thereof.

Statement 237: A method of treating an infectious disease in a subject in need thereof, the method comprising: administering to the subject a pharmaceutically effective amount of the combination therapy composition according to any one of Statements 33-78; wherein the label provides an advantageous therapeutic effect in treating the infectious disease.

Statement 238: The method according to Statement 237, wherein the label is a radiotherapeutic label capable of delivering radiation to an infected tissue in the subject and the advantageous therapeutic effect is increased viral particle inactivation, reduced viral replication, and/or reduced viral load in the tissue.

Statement 239: The method according to Statement 238, wherein the label is selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof.

Statement 240: The method according to Statement 237, wherein the label is a non-radioactive metal that is toxic to an infectious diseases causing agent and the advantageous therapeutic effect is toxicity-induced cell death or viral particle inactivation, reduced viral replication, and/or reduced viral load in the tissue.

Statement 241: The method according to Statement 240, wherein the non-radioactive metal is selected from the group consisting of rhenium, platinum, copper, iron, arsenic, lead, tantalum, and any combination thereof.

Statement 242: A combination therapy method of treating an infectious disease in a subject in need thereof, the method comprising: administering to the subject a pharmaceutically effective amount of the combination therapy composition according to any one of Statements 1-32; administering to the subject a therapeutically effective amount of a radiotherapeutic regimen; wherein the radiotherapeutic regimen delivers radiation to an infected tissue in the subject in need of treatment.

Statement 243: The method according to Statement 242, wherein the radiotherapeutic regimen causes increased viral particle inactivation, reduced viral replication, and/or reduced viral load in the tissue.

Statement 244: The method according to Statement 243, wherein the radiotherapeutic regimen comprises administration of a radioactive agent selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof.

Statement 245: The method according to any one of Statements 242-243, wherein the at least one active pharmaceutical ingredient is an antiviral compound.

Statement 246: The method according to Statement 245, wherein the antiviral is selected from the group consisting of remdesivir, oseltamivir phosphate, zanamivir, peramivir, baloxavir marboxil, darunavir, atazanavir, ritonavir, acyclovir, valacyclovir, valganciclovir, tenofovir, raltegravir, viral attachment inhibitors, viral entry inhibitors, uncoating inhibitors, protease inhibitors, polymerase inhibitors, nucleoside and nucleotide reverse transcriptase inhibitors, nonnucleoside reverse-transcriptase inhibitors, integrase inhibitors, and any combination thereof.

Statement 247: The method according to any one of Statements 242-246, wherein the infectious disease is a viral infection.

Statement 248: The method according to any one of Statements 242-246, wherein the infectious disease is a respiratory viral infection selected from the group consisting of human influenza, the common cold, Middle East respiratory syndrome (MERS), severe acute respiratory syndrome coronavirus (SARS), and COVID-19.

Statement 249: The method according to any one of Statements 242-246, wherein the infectious disease is caused by infection by a virus selected from the group consisting of severe acute respiratory syndrome coronavirus (SARS-CoV), severe acute respiratory syndrome coronavirus 2 (SARS-CoV-2), Middle East respiratory syndrome-related coronavirus (MERS-CoV), human coronavirus NL63 (HCoV NL63), human coronavirus OC43 (HCoV-OC43), human coronavirus HKU1 (HCoV HKU1), and human coronavirus 229E (HCoV-229E).

What is claimed is:

1. A combination therapy composition comprising:
    a cannabinoid compound-chelator-label-nucleoside analog conjugate comprising a structure according to Formula IV:

Formula IV

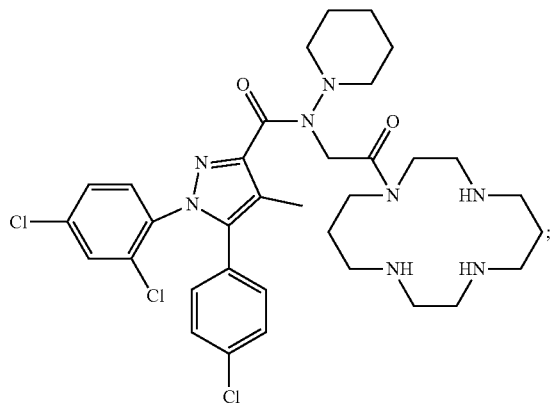

and
a chelator-label-nucleoside analog conjugate comprising a structure according to Formula I:

Formula I

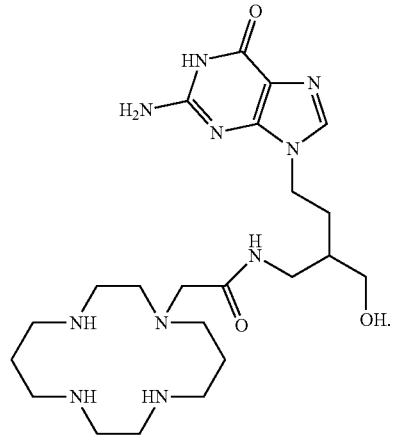

2. The combination therapy composition according to claim 1, wherein the label of each of the cannabinoid compound-chelator-label-nucleoside analog conjugate and the chelator-label-nucleoside analog conjugate is independently selected from the group consisting of Technetium-99, Gallium-68, Copper-60, Copper-64, Indium-111, Holmium-166, Rhenium-186, Rhenium-188, Yttrium-90, Lutetium-177, Radium-223, Actinium-225, and any combination thereof.

3. The combination therapy composition according to claim 1, further comprising an analgesic selected from the group consisting of nonsteroidal anti-inflammatory drugs (NSAIDs), aspirin, ibuprofen, acetaminophen, naproxen, codeine, salicylates, narcotic analgesics, cyclooxygenase-2 (cox-2) inhibitors, calcitonin gene-related peptide (CGRP) inhibitors, opioids, ziconotide, hydrocodone, oxycodone, fentanyl, morphine, oxymorphone, buprenorphine, levorphanol, tramadol, hydromorphone, methadone, meperidine, propoxyphene, nalbuphine, and any combination thereof.

4. The combination therapy composition according to claim 1, further comprising an antiviral selected from the group consisting of remdesivir, oseltamivir phosphate, zanamivir, peramivir, baloxavir marboxil, darunavir, atazanavir, ritonavir, acyclovir, valacyclovir, valganciclovir, tenofovir, raltegravir, viral attachment inhibitors, viral entry inhibitors, uncoating inhibitors, protease inhibitors, polymerase inhibitors, nucleoside and nucleotide reverse transcriptase inhibitors, nonnucleoside reverse-transcriptase inhibitors, integrase inhibitors, and any combination thereof.

5. A method of treating an infectious disease in a subject in need thereof, the method comprising:
    administering to the subject a pharmaceutically effective amount of the combination therapy composition according to claim 1;
    wherein the combination therapy composition produces at least one synergistic therapeutic effect when administered to a subject, the synergistic therapeutic effect selected from the group consisting of reduced observed toxicity of the at least one of the cannabinoid compound-chelator-label-nucleoside analog conjugate and the chelator-label-nucleoside analog conjugate, reduction in the administration dosage or amount of at least one of the cannabinoid compound-chelator-label-nucleoside analog conjugate and the chelator-labelnucleoside analog conjugate required to obtain an advantageous clinical outcome, improved clinical outcomes of the combination therapy as compared to the separate administration of the cannabinoid compound-chelator-label-nucleoside analog conjugate and the chelator-label-nucleoside analog conjugate, and any combination thereof;

wherein the infectious disease is caused by infection by a virus selected from the group consisting of severe acute respiratory syndrome coronavirus (SARS-CoV), severe acute respiratory syndrome coronavirus 2 (SARS-CoV-2), Middle East respiratory syndrome-related coronavirus (MERS-CoV), human coronavirus NL63 (HCoV NL63), human coronavirus OC43 (HCoV-OC43), human coronavirus HKU1 (HCoV HKU1), and human coronavirus 229E (HCoV-229E).

6. The method according to claim 5, further comprising:

performing an imaging technique on the subject or a portion thereof, wherein the imaging technique is capable of detecting one or more signals from the combination therapy composition to generate one or more data images, wherein the imaging technique is selected from the group consisting of positron emission tomography (PET), computed tomography (CT), single photon emission computed tomography (SPECT), magnetic resonance imaging (MRI), near-infrared (NIR), optical imaging, optoacoustic imaging, ultrasound, and any combination thereof;

making at least one treatment decision based on the one or more data images, wherein the at least one treatment decision is selected from the group consisting of raising or lowering the dose of combination therapy composition administered to the subject, determining an optimal dosage of administration for the particular subject based on the one or more data images, determining whether a dysfunctional pathway or tissue of interest associated with a disease was successfully targeted by the combination therapy composition, determining if an adverse advent was caused by administration of the combination therapy composition, and any combination thereof; and monitoring the uptake of one or more components of the combination therapy composition based on the one or more data images, wherein the one or more data images provides for visual assessment of uptake at a tissue site of interest of one or more components of the combination therapy composition.

* * * * *